United States Patent
Farritor et al.

(10) Patent No.: US 10,667,883 B2
(45) Date of Patent: Jun. 2, 2020

(54) ROBOTIC SURGICAL DEVICES, SYSTEMS, AND RELATED METHODS

(71) Applicant: Virtual Incision Corporation, Lincoln, NE (US)

(72) Inventors: Shane Farritor, Lincoln, NE (US); Chris Santoro, Brooklyn, NY (US); Jeff Shasho, Brooklyn, NY (US); Nishant Kumar, Bergenfield, NJ (US); Mateusz Szczesiak, Forest Hills, NY (US); Jason Herman, East Northport, NY (US)

(73) Assignee: Virtual Incision Corporation, Lincoln, NE (US)

( * ) Notice: Subject to any disclaimer, the term of this patent is extended or adjusted under 35 U.S.C. 154(b) by 189 days.

(21) Appl. No.: 14/212,686

(22) Filed: Mar. 14, 2014

(65) Prior Publication Data

US 2014/0303434 A1 Oct. 9, 2014

Related U.S. Application Data

(60) Provisional application No. 61/792,508, filed on Mar. 15, 2013.

(51) Int. Cl.
- *A61B 90/35* (2016.01)
- *A61B 17/29* (2006.01)

(Continued)

(52) U.S. Cl.
CPC .......... *A61B 90/35* (2016.02); *A61B 1/00149* (2013.01); *A61B 1/3132* (2013.01);

(Continued)

(58) Field of Classification Search
CPC ............ A61B 19/2203; A61B 1/00149; A61B 1/3132; A61B 117/29; A61B 17/3423;

(Continued)

(56) References Cited

U.S. PATENT DOCUMENTS

| 3,870,264 A | 3/1975 | Robinson |
| 3,989,952 A | 11/1976 | Timberlake et al. |

(Continued)

FOREIGN PATENT DOCUMENTS

| CN | 1082821918 | 12/2012 |
| DE | 102010040405 | 3/2012 |

(Continued)

OTHER PUBLICATIONS

Abbott et al., "Design of an Endoluminal Notes Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Carl H Layno
*Assistant Examiner* — Dacheng Xie
(74) *Attorney, Agent, or Firm* — Davis, Brown, Koehn, Shors & Roberts, P.C.; Sean D. Solberg

(57) ABSTRACT

The embodiments disclosed herein relate to various medical device components, including components that can be incorporated into robotic and/or in vivo medical devices. Certain embodiments include various modular medical devices for in vivo medical procedures.

18 Claims, 21 Drawing Sheets

(51) Int. Cl.
  *A61B 1/00* (2006.01)
  *A61B 17/34* (2006.01)
  *A61B 1/313* (2006.01)
  *A61B 34/30* (2016.01)
  *A61B 46/10* (2016.01)
  *A61B 90/50* (2016.01)
  *A61B 90/30* (2016.01)
  *A61B 90/00* (2016.01)

(52) U.S. Cl.
  CPC .......... *A61B 17/29* (2013.01); *A61B 17/3423* (2013.01); *A61B 34/30* (2016.02); *A61B 46/10* (2016.02); *A61B 90/50* (2016.02); *A61B 90/30* (2016.02); *A61B 90/361* (2016.02); *A61B 2034/302* (2016.02); *A61B 2034/305* (2016.02)

(58) Field of Classification Search
  CPC .............. A61B 19/081; A61B 19/5212; A61B 2019/2215; A61B 2019/2234; A51B 19/5202
  See application file for complete search history.

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A * | 5/1990 | Kawai .................. B25J 9/0084 29/402.08 |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Ortiz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |

(56) References Cited

U.S. PATENT DOCUMENTS

| | | |
|---|---|---|
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |

(56) References Cited

U.S. PATENT DOCUMENTS

| | | |
|---|---|---|
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 8,604,742 B2 | 12/2013 | Farritor et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Khalili et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1* | 1/2008 | Solomon ............ A61B 19/2203 606/1 |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |

(56) References Cited

U.S. PATENT DOCUMENTS

| | | |
|---|---|---|
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1* | 6/2009 | Yeung ............ A61B 19/2203 606/130 |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1* | 3/2010 | Miller ............ A61B 17/320068 606/169 |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0204713 A1 | 8/2010 | Ruiz |
| 2010/0245549 A1 | 9/2010 | Allen et al. |
| 2010/0262162 A1 | 10/2010 | Omori |
| 2010/0274079 A1* | 10/2010 | Kim ................... A61B 1/00147 600/102 |
| 2010/0292691 A1 | 11/2010 | Brogna |
| 2010/0301095 A1* | 12/2010 | Shelton, IV ............ A61B 17/00 227/175.4 |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0082365 A1 | 4/2011 | McGrogan et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1* | 9/2011 | Ranjit ............ A61B 19/2203 606/130 |
| 2011/0264078 A1 | 10/2011 | Lipow |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0041360 A1 | 2/2013 | Farritor |
| 2013/0131695 A1* | 5/2013 | Scarfogliero ...... A61B 19/2203 606/130 |
| 2013/0345717 A1 | 5/2013 | Scarfogliero et al. |
| 2014/0046340 A1 | 2/2014 | Wilson et al. |
| 2014/0058205 A1 | 2/2014 | Frederick et al. |
| 2014/0039515 A1 | 6/2014 | Mondry et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 1992/21291 | 5/1991 |
| WO | WO 2011/118646 A1 | 9/2001 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005009211 | 2/2005 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO201050771 A2 | 5/2010 |
| WO | 2011135503 A1 | 11/2011 |
| WO | WO 2011/135503 A1 | 11/2011 |
| WO | WO 2011135503 | 11/2011 |
| WO | WO 2011075693 | 7/2012 |
| WO | 2013009887 A1 | 1/2013 |
| WO | WO 2013009887 | 1/2013 |
| WO | WO 2014011238 | 1/2014 |
| WO | 2014144220 A1 | 9/2014 |

OTHER PUBLICATIONS

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Applicant Amendment after Notice of Allowance under Rule 312, filed Aug. 25, 2008, in related case U.S. Appl. No. 11/695,944, 6pp.

Applicant Response to Office Action dated Apr. 17, 2007, in related case U.S. Appl. No. 11/552,379, filed Aug. 8, 2007, 7 pp.

Applicant Response to Office Action dated Aug. 18, 2006, in related case U.S. Appl. No. 11/398,174, filed Nov. 7, 2006, 8pp.

Applicant Response to Office Action dated Aug. 21, 2006, in related case U.S. Appl. No. 11/403,756, filed Nov. 21, 2006, 52pp.

Applicant Response to Office Action dated Oct. 29, 2007, in related case U.S. Appl. No. 11/695,944, filed Jan. 22, 2008, 6pp.

Atmel 80C5X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4): 325-330.

(56) References Cited

OTHER PUBLICATIONS

Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al, "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," in McLaughliin, M.L., Hespanha, J.P., and Sukhatme, G., editors. Touch in virtual environments, IMSC Series in Multimedia 2001, 28pp.
Cavusoglu et al., " Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., " Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May, 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1.
International Preliminary Report on Patentability from related case PCT/US2007/014567, dated Jan. 8, 2009, 11 pp.
International Search report and Written Opinion from international application No. PCT/US2012/41911, dated Mar. 13, 2013.
International Search Report and Written Opinion from international application No. PCT/US12/46274, dated Sep. 25, 2012.
International Search Report and Written Opinion from international application No. PCT/US2007/089191, dated Nov. 10, 2008, 20 pp.
"International Search Report and Written Opinion from international application No. PCT/US07/14567, dated Apr. 28, 2008, 19 pp."
International Search Report and Written Opinion of international application No. PCT/US2008/069822, dated Aug. 5, 2009, 12 pp.
International Search Report and Written Opinion of international application No. PCT/US2008/073334, dated Jan. 12, 2009, 11 pp.
International Search Report and Written Opinion of international application No. PCT/US2008/073369, dated Nov. 12, 2008, 12 pp.
International Search Report and Written Opinion issued in PCT/US11/46809, dated Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al, "Force-Feedback Grasper Helps Restore the Sense of Touch in Minimally Invasive Surgery," Journal of Gastrointestinal Surgery, 1999; 3: 278-285.

(56) References Cited

OTHER PUBLICATIONS

Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al, "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Svstems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al, "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al, "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Palm, William, "Rapid Prototyping Primer" May 1998 (revised Jul. 30, 2002) (http://www.me.psu.edu/lamancusa/rapidpro/primer/chapter2.htm).
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Guo et al., "Fish-like Underwater Microrobot with 3 DOF," Proceedings of the 2002 IEEE International Conference on Robotics & Automation, May 2002: 738-743.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al, "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.
Platt et al, "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile in Vivo Biopsy and Camera Robot," Studies in Health and Infonnatics Medicine Meets Virtual Reality, vol. 119., pp. 449-454, IOS Press, Long Beach, CA, 2006e.
Rentschler et al., Mobile In Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp, I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of in Vivo Wheeled Robotic Mobility," IEEE Transactions on Robotics, 22 (2): 308-321, 2005c.

(56) References Cited

OTHER PUBLICATIONS

Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Informatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics-Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics-Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al, "Robot-Assisted surgical systems: a new era in laparoscopic surgery," Ann R. Coll Surg Engl., 2002; 84: 223-226.
Ruurda et al, "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al, "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining, " vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4): 477-483.
Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.

* cited by examiner

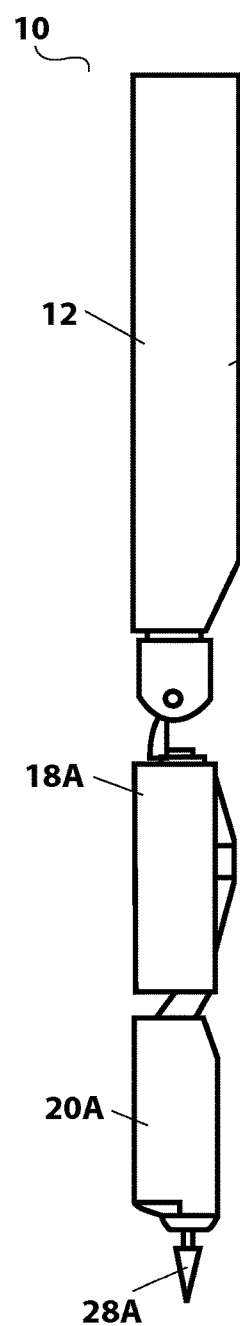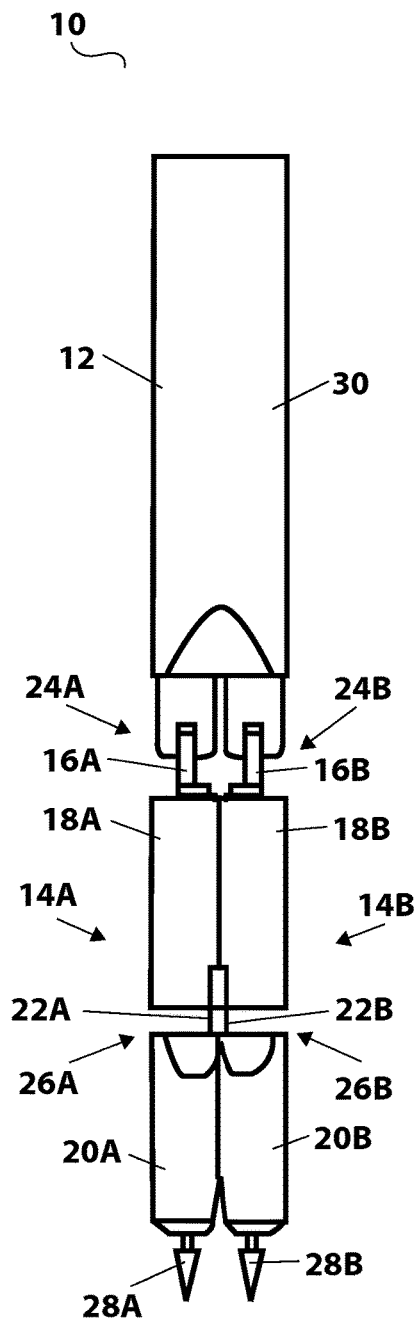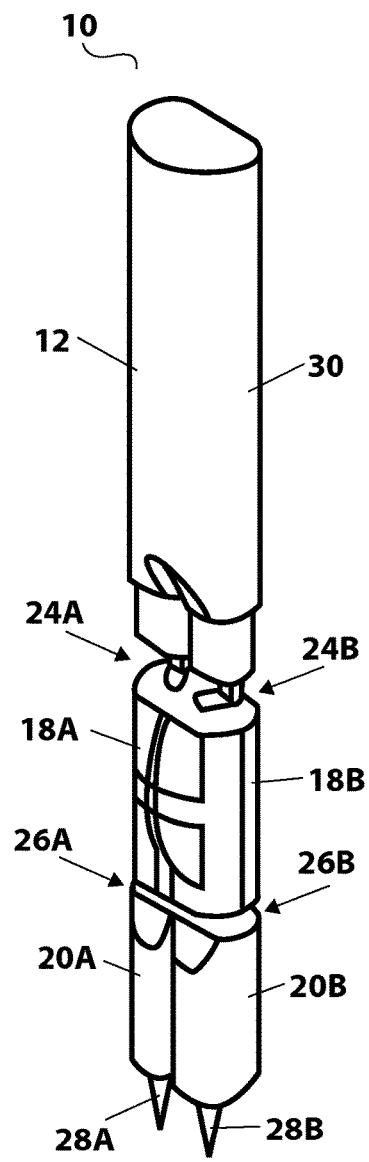
Figure 1A  Figure 1B  Figure 1C
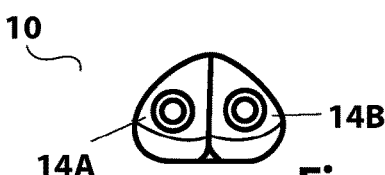
Figure 1D

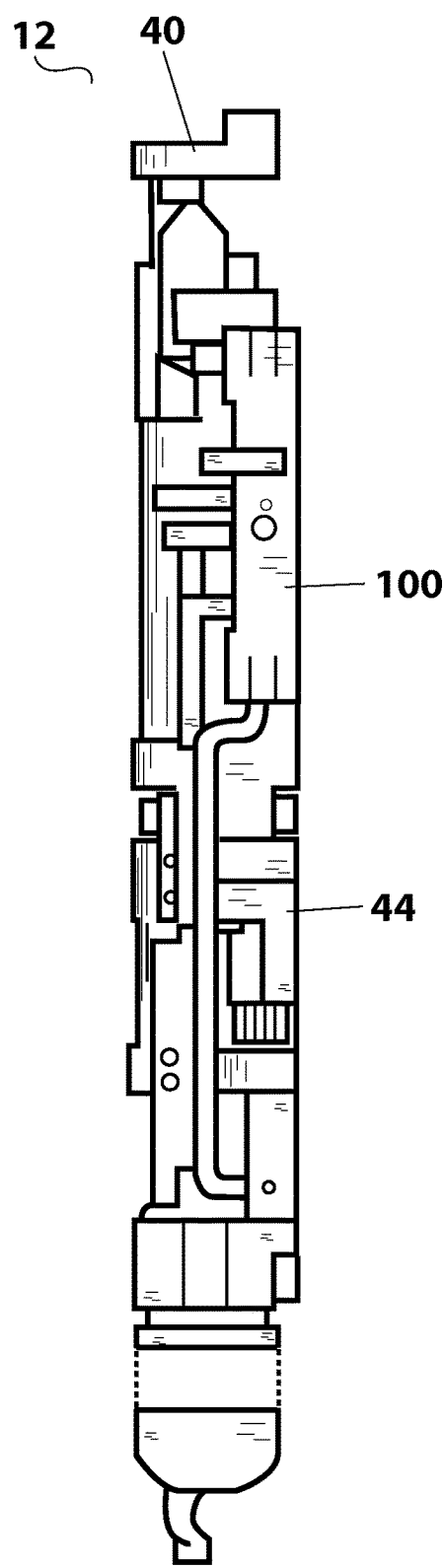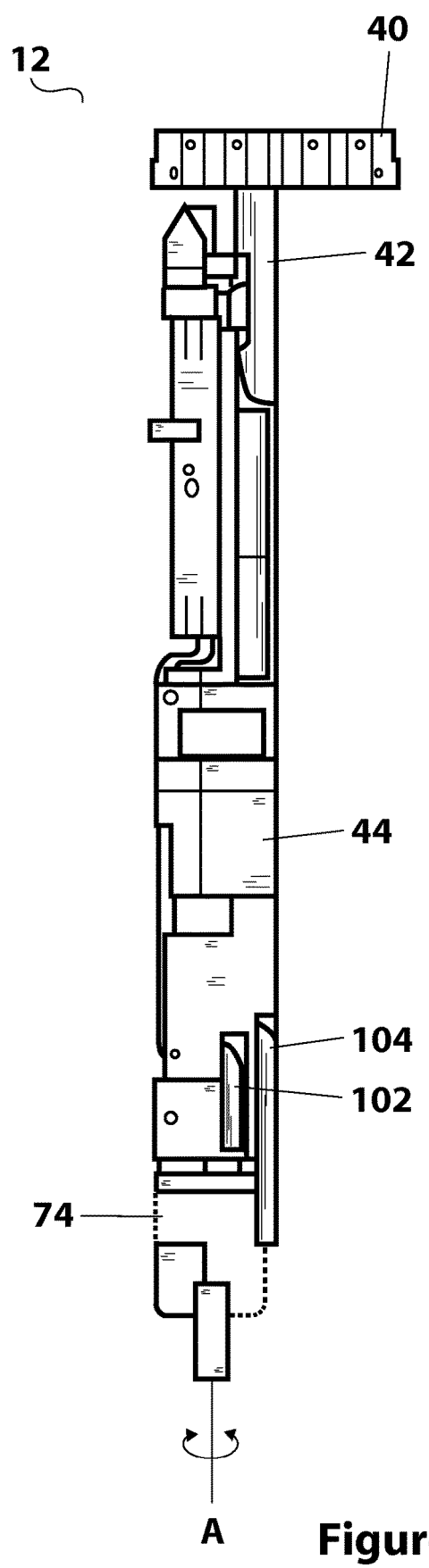
Figure 2A
Figure 2B

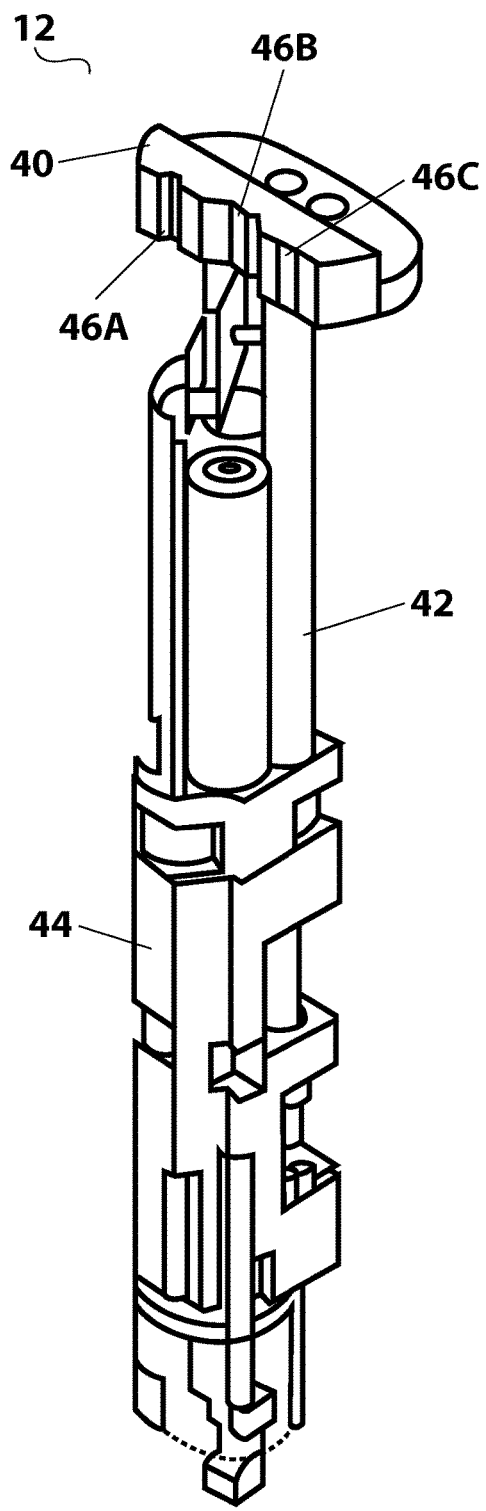
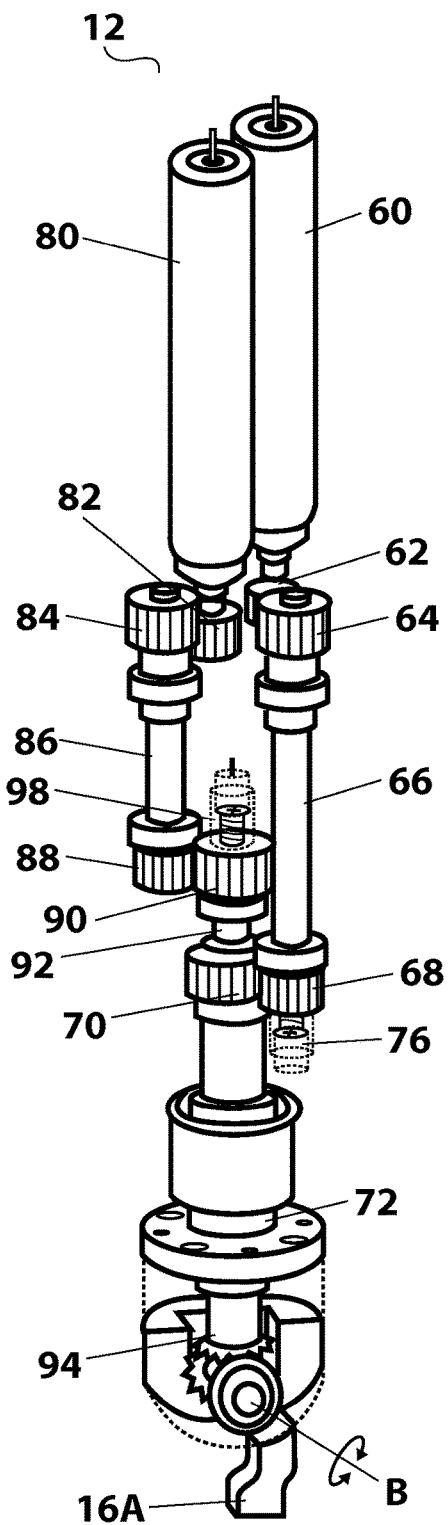
Figure 2C
Figure 2D

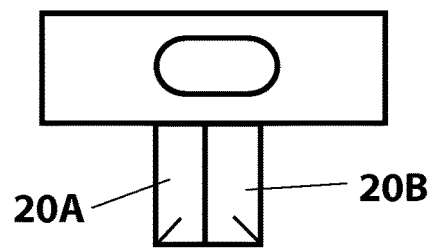
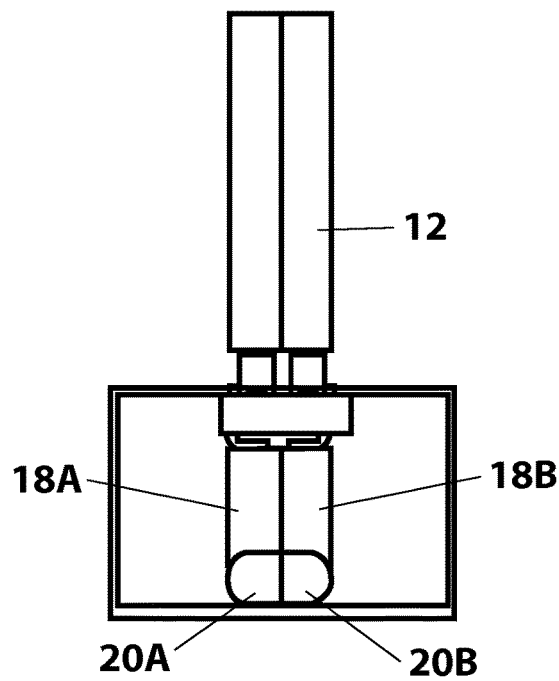
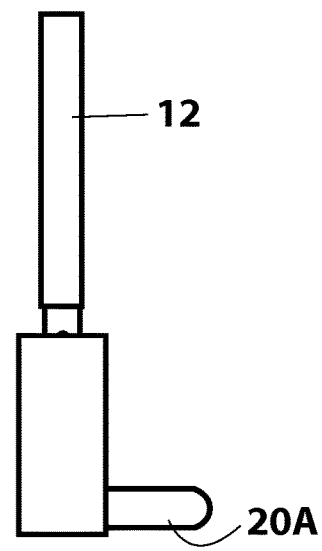
Figure 14A
Figure 14B
Figure 14C
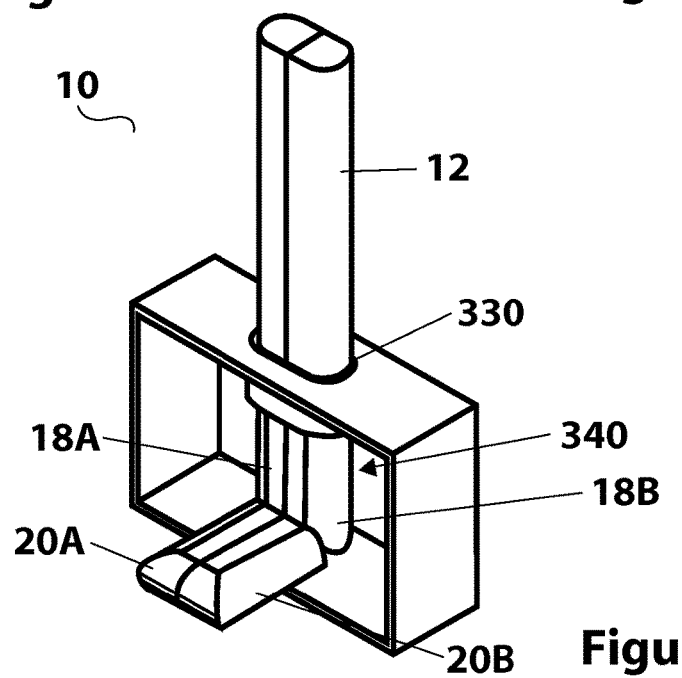
Figure 14D

ROBOTIC SURGICAL DEVICES, SYSTEMS, AND RELATED METHODS

CROSS REFERENCE TO RELATED APPLICATIONS

This application claims priority from U.S. Provisional Application 61/792,508, filed Mar. 15, 2013, and entitled "Single Site Robotic Surgical Devices, Systems and Methods," which is hereby incorporated herein by reference in its entirety.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods of operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF DESCRIPTION OF THE DRAWINGS

FIG. 1A is a side view of a robotic surgical device according to one embodiment.

FIG. 1B is perspective front view of the device of FIG. 1.

FIG. 1C is a perspective view of the device of FIG. 1.

FIG. 1D is an end view of the device of FIG. 1.

FIG. 2A is a cutaway view of the interior body and shoulder of the robotic medical device, according to one embodiment.

FIG. 2B is a rotated cutaway view of the robotic medical device of FIG. 2A.

FIG. 2C is a perspective cutaway view of the medical device, according to the embodiment of FIG. 2A.

FIG. 2D is a further cutaway perspective view of the medical device body, according to the embodiment of FIG. 2A.

FIG. 14A depicts a top view of a robotic device during insertion, according to one embodiment.

FIG. 14B is a front view of the device of FIG. 14A.

FIG. 14C is a side view of the device of FIG. 14A.

FIG. 14D is a perspective view of the device of FIG. 14A.

DETAILED DESCRIPTION

Figure 2E:
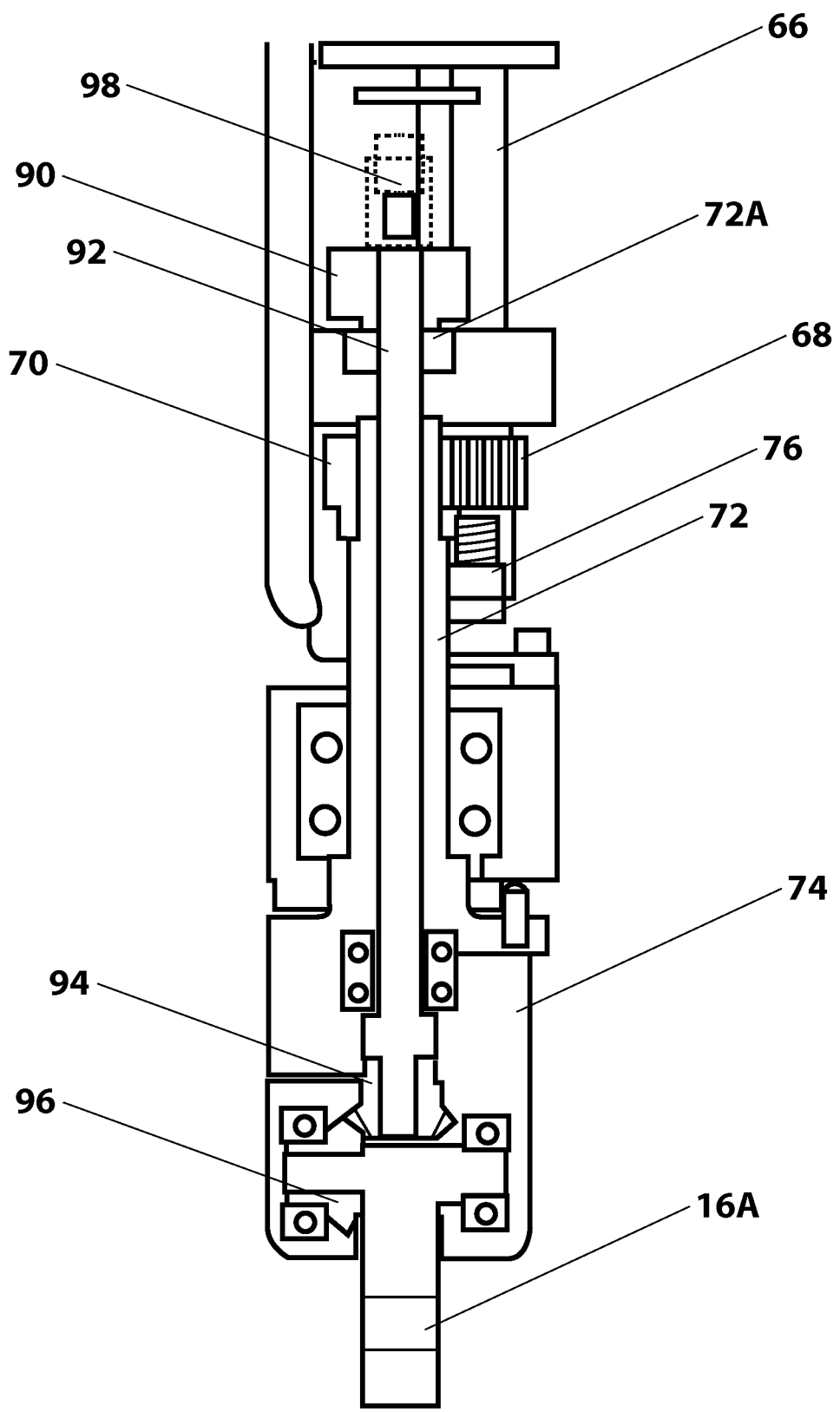
FIG. 2E is a cutaway view of the lower body and shoulder of a robotic device, according to the embodiment of FIG. 2A.

The various systems and devices disclosed herein relate to devices for use in medical procedures and systems. More specifically, various embodiments relate to various medical devices, including robotic devices and related methods and systems. Certain implementations relate to such devices for use in laparo-endoscopic single-site (LESS) surgical procedures.

It is understood that the various embodiments of robotic devices and related methods and systems disclosed herein can be incorporated into or used with any other known medical devices, systems, and methods. It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), and Ser. No. 13/738,706 (filed Jan. 10, 2013 and entitled "Methods, Systems, and Devices for Surgical Access and Insertion"), and U.S. Pat. No. 7,492,116 (filed on Apr. 3, 2007 and entitled "Robot for Surgical Applications"), U.S. Pat. No. 7,772,796 (filed on Nov. 29, 2007 and entitled "Robot for Surgical Applications"), U.S. Pat. No. 8,179,073 (issued May 15, 2012, and entitled "Robotic Devices with Agent Delivery Components and Related Methods"), U.S. Pat. No. 8,343,171 (filed on Jul. 11, 2008 and entitled "Methods and Systems of Actuation in Robotic Devices"), and U.S. Pat. No. 8,679,096 (filed Nov. 26, 2008 and entitled "Multifunctional Operational Component for Robotic Devices"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command from an external console or control system, as has been described previously.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

As shown generally in FIGS. 1A, 1B, 1C, and 1D, certain exemplary embodiments relate to a device 10 having a body 12 with two arms 14A, 14B operably coupled thereto. The body 12 as shown further comprises a casing 30. The body 12 is also referred to as a "device body." Each arm 14A, 14B has a first coupling link 16A, 16B that couples the arm 14A, 14B to the body 12.

As is best shown in FIGS. 1B-1C, this first coupling link 16A, 16B can also be referred to herein as a "first coupling component" or "shoulder link" and is part of the first rotatable joint 24A, 24B (also referred to herein as the "shoulder joint"). Each arm 14A, 14B has an upper arm (also referred to herein as an "inner arm," "inner arm assembly," "inner link," "inner link assembly," "upper arm assembly," "first link," or "first link assembly") 18A, 18B, and a forearm (also referred to herein as an "outer arm," "outer arm assembly," "outer link," "outer link assembly," "forearm assembly," "second link," or "second link assembly") 20A, 20B.

As is shown in FIGS. 1A-1C and further discussed in relation to FIGS. 12-17 below, the upper arms 18A, 18B are rotatably coupled to the coupling links 16A, 16B, which are rotatably coupled to the body 12. Each arm 14A, 14B has a second coupling link 22A, 22B that couples the upper arm 18A, 18B to the forearm 20A, 20B. This second coupling link 22A, 22B can also be referred to herein as a "second coupling component" or "elbow link" and is part of the second rotatable joint 26A, 26B (also referred to herein as the "elbow joint"). More specifically, in the right arm 14A, the upper arm 18A is rotatably coupled to the forearm 20A at the elbow joint 26A via the elbow link 22A, while in the left arm 14B, the upper arm 18B is rotatably coupled to the forearm 20B at the elbow joint 26B via elbow link 22B.

As shown, each of the arms 14A, 14B also has an end effector 28A, 28B operably coupled to the distal end of the forearm 20A, 20B. An end effector can also be referred to herein as an "operational component."

In one implementation, each of the arms 14A, 14B has six degrees of freedom. That is, as explained in further detail below, each arm 14A, 14B has three degrees of freedom at the shoulder, one degree of freedom at the elbow, and two degrees of freedom at the end effector (which can be rotated—end effector roll—and opened/closed). As such, the six degrees of freedom of each arm 14A, 14B are analogous to the degrees of freedom of a human arm, which also has three degrees of freedom at the shoulder and one at the elbow. One advantage of an arm having four degrees of freedom (with an end effector having two degrees of freedom) is that the end effector can have multiple orientations at the same Cartesian point. This added dexterity allows the surgeon or other user more freedom and a more intuitive sense of control while operating the device.

The internal components of the body 12 are depicted in the various embodiments shown in FIGS. 2A, 2B, 2C, 2D, and 2E. The body 12 is shown in these figures without its casing 30. More specifically, these figures depict the right half of the body 12 and the internal components that control/actuate the right arm 14A. It is to be understood that the internal components in the left half (not shown) that operate/control/actuate the left arm 14B are substantially the same as those depicted and described herein and that the descriptions provided below apply equally to those components as well.

FIGS. 2A, 2B, and 2C include the internal structural or support components of the body 12. In one implementation, the body 12 has an internal top cap 40, an internal support rod 42, and an internal support chassis 44, as shown. The support rod 42 couples the top cap 40 to the support chassis 44. In certain embodiments, the support chassis comprises an aluminum structure. In alternate embodiments, an injection-molded polymer may be used. These components maintain the structure of the body 12 and provide structural support for the components disposed therein, and in certain embodiments are surrounded by a housing or shell. According to one embodiment, the internal top cap 40 defines three partial lumens 46A, 46B, 46C as best shown in FIG. 2C. The top cap 40 couples to the body casing 30 such that each of the partial lumens 46A, 46B, 46C is formed into a full lumen defined by the coupling of the cap 40 and casing 30. As will be described in further detail below, these lumens 46A, 46B, 46C can be configured to receive various wires, cords, or other components to be inserted into or through the body 12.

In contrast to FIGS. 2A-2C, FIG. 2D depicts the internal actuation and control components of the right half of the body 12 with the internal structural or support components hidden in order to better display the internal actuation and control components. These internal actuation and control components are configured to provide two degrees of freedom at the shoulder joint 24A.

FIG. 2E is an enlarged view of the distal end of the body 12. In one embodiment, certain of the internal components depicted in FIGS. 2D and 2E are configured to actuate rotation at the shoulder joint 24A around axis A (as best shown in FIG. 2B), which is parallel to the longitudinal axis of the body 12. This rotation around axis A is also referred to as "yaw" or "shoulder yaw." The rotation, in one aspect, is created as follows. An actuator 60 is provided that is, in this implementation, a motor assembly 60. The motor assembly 60 is operably coupled to the proximal motor gear 62, which is coupled to the proximal driven gear 64 such that rotation of the proximal motor gear 62 causes rotation of the proximal driven gear 64. The proximal driven gear 64 is fixedly coupled to a proximal transmission shaft 66, which has a distal transmission gear 68 at the opposite end of the shaft 66. The distal transmission gear 68 is coupled to a distal driven gear 70, which is fixedly coupled to the distal transmission shaft 72. A magnet holder 76 containing a magnet is also operably coupled to the distal transmission gear 68. The holder 76 and magnet are operably coupled to a magnetic encoder (not shown).

It is understood that the magnet holder 76, magnet, and magnetic encoder (and those similar components as discussed elsewhere herein in relation to other joints) are components of an absolute position sensor that is the same as or substantially similar to one or more of the absolute position sensors disclosed in U.S. application Ser. No. 13/573,849 filed Oct. 9, 2012, and Ser. No. 13/833,605 filed Mar. 15, 2013, which are hereby incorporated by reference in their entirety. The distal transmission shaft 72 is fixedly coupled at its distal end to a rotatable pitch housing 74 (as best shown in FIGS. 2B and 2E) such that rotation of the distal driven gear 70 causes rotation of the shaft 72 and thus rotation of the housing 74 around axis A as shown in FIG. 2B.

According to one implementation, certain other internal components depicted in FIG. 2D are configured to actuate rotation at the shoulder joint 24A around axis B (as best shown in FIG. 2D), which is perpendicular to the longitudinal axis of the body 12. This rotation around axis B is also referred to as "pitch" or "shoulder pitch." The rotation, in one embodiment, is created as follows. An actuator 80 is provided that is, in this implementation, a proximal shoulder motor assembly 80. The motor assembly 80 is operably coupled to a proximal shoulder motor gear 82, which is coupled to the proximal shoulder driven gear 84 such that rotation of the proximal shoulder motor gear 82 causes rotation of the proximal shoulder driven gear 84. This driven gear 84 is fixedly coupled to a proximal shoulder transmission shaft 86, which has a proximal shoulder transmission gear 88 at the opposite end of the shaft 86.

The proximal transmission gear 88 is coupled to a distal shoulder driven gear 90, which is fixedly coupled to the distal shoulder shaft 92. A magnet holder 98 containing a magnet is also operably coupled to the driven gear 90. The holder 98 and magnet are operably coupled to a magnetic encoder (not shown). As best shown in FIG. 2E, a portion of the distal shoulder shaft 92 is disposed within the lumen 72A of the shaft 72 described above and extends out of the distal end of the shaft 72 into the housing 74. As best shown in FIG. 2E, the distal end of the shaft 92 is coupled to a rotation gear 94 that is a bevel gear 94. The rotation gear 94 is operably coupled to link gear 96, which is also a bevel gear 96 according to one implementation. The link gear 96 is operably coupled to the shoulder link 16A (discussed above) such that rotation of the shaft 92 causes rotation of the rotation gear 94 and thereby the rotation of the link gear 96 and thus rotation of the link 16A around axis B as best shown in FIG. 2D.

In this embodiment, the two axes of rotation are coupled. That is, if solely rotation around axis A (pure yaw) is desired, then the "pitch drive train" (the motor 80 and all coupled gears and components required to achieve rotation around axis B) must match the speed of the "yaw drive train" (the motor 60 and all coupled gears and components required to achieve rotation around axis A) such that there is no relative angular displacement between the pitch housing 74 and the rotation gear 94. In contrast, if solely rotation around axis B (pure pitch) is desired, then the yaw drive train must hold position while the pitch drive train is actuated.

In one implementation as shown in FIG. 2A, the body 12 has a rigid-flex PCB 100 positioned in the body. The PCB 100 is operably coupled to and communicates with the motors 60, 80 and magnetic encoders (not shown) to perform the yaw and pitch functions.

According to another embodiment, at least one connection component is associated with the body 12. More specifically, in this implementation, a power/communication line 102 and a cautery power line 104 are coupled at their proximal ends to one or more external power sources (not shown) and extend into the device 10 through one or more of the three lumens 46A, 46B, 46C defined partially by internal top cap 40. The lines 102, 104 extend through the body 12 and exit as shown in FIG. 2B and extend to the upper arm segment. In certain embodiments, the lines 102, 104 are not continuous, but occur in series. In certain of these embodiments, the lines contain terminus at various PCB boards. In yet further embodiments of the lines may run in parallel.

In one embodiment, the body 12 can be coupled at its proximal end to a positioning rod (also referred to as an "insertion rod") (not shown). It is understood that the positioning rod can be any such known component for helping to position the device 10 and/or maintain and stabilize the position of the device 10. According to one implementation, the power/communication line 102 and/or the cautery power line 104 can extend proximally through one or more lumens in the positioning rod.

In one embodiment, any of the motors discussed and depicted herein can be brush or brushless motors, such as brushless DC motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass.

FIGS. 3A, 3B, 3C, 3D, 3E, 4A, 4B, 4C, 4D, and 4E according to one embodiment, depict the internal components of the right upper arm 18A, which is shown in these figures without its casing. More specifically, these figures depict the right arm 14A and the internal components therein. It is understood that the internal components in the left upper arm 18B are substantially the same as those depicted and described herein and that the descriptions provided below apply equally to those components as well.

FIGS. 3A-3E depict the internal components of the right upper arm 18A, including actuators, drive components, and electronics, with the internal structural or support components hidden in order to better display the internal components. In contrast to FIGS. 3A-3E, FIGS. 4A-4E include both the internal actuator, drive, and electronics components, but also the internal structural or support components of the right upper arm 18A.

Figure 3A:
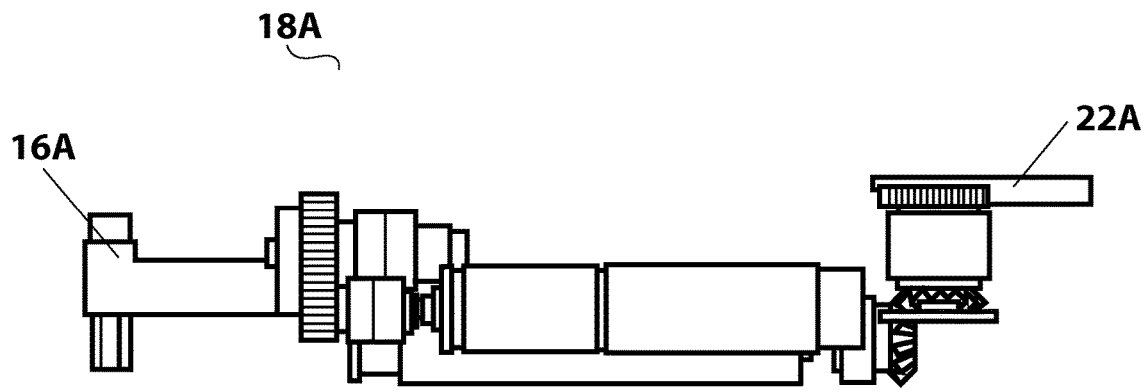
FIG. 3A is a cutaway side view of the upper arm of the robotic medical device, according to one embodiment.
Figure 3B:
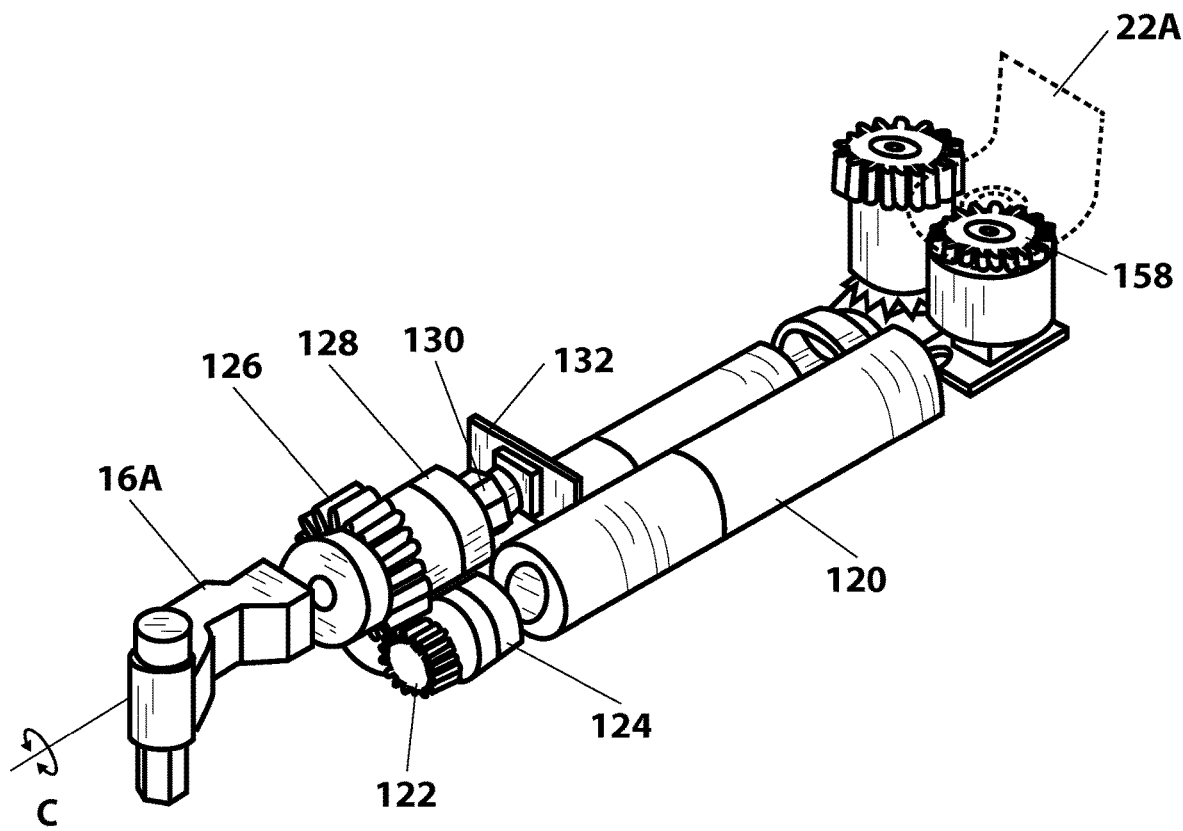
FIG. 3B is a perspective view of the embodiment of FIG. 3A.

In one embodiment, certain of the internal components depicted in FIGS. 3A-3E are configured to actuate rotation at the shoulder link 16A around axis C (as best shown in FIG. 3B), which is parallel to the longitudinal axis of the right upper arm 18A. This rotation around axis C is also referred to as "shoulder roll." The rotation, in one aspect, is created as follows: a first shoulder actuator 120 is provided that is, in this implementation, a motor assembly 120. This motor assembly 120 is operably coupled to a first shoulder motor gear 122. This motor gear 122 is supported by a first shoulder bearing pair 124. This motor gear 122 is coupled to the shoulder driven gear 126 such that rotation of the first shoulder motor gear 122 causes rotation of the driven gear 126. The driven gear 126 is fixedly coupled to the shoulder link 16A such that rotation of the driven gear 126 causes rotation of the shoulder link 16A around axis C as shown in FIG. 3B. The driven gear 126 is supported by a second bearing pair 128. A magnet holder 130 further comprising a magnet is also operably coupled to the driven gear 126. The holder 130 and magnet are operably coupled to a magnetic encoder 132.

The rotation of the shoulder link 16A around axis C causes the right upper arm 18A (and thus the forearm 20A) to rotate in relation to the body 12. According to one embodiment, this rotation adds an additional degree of freedom not provided in prior two-armed surgical devices.

Figure 3C:
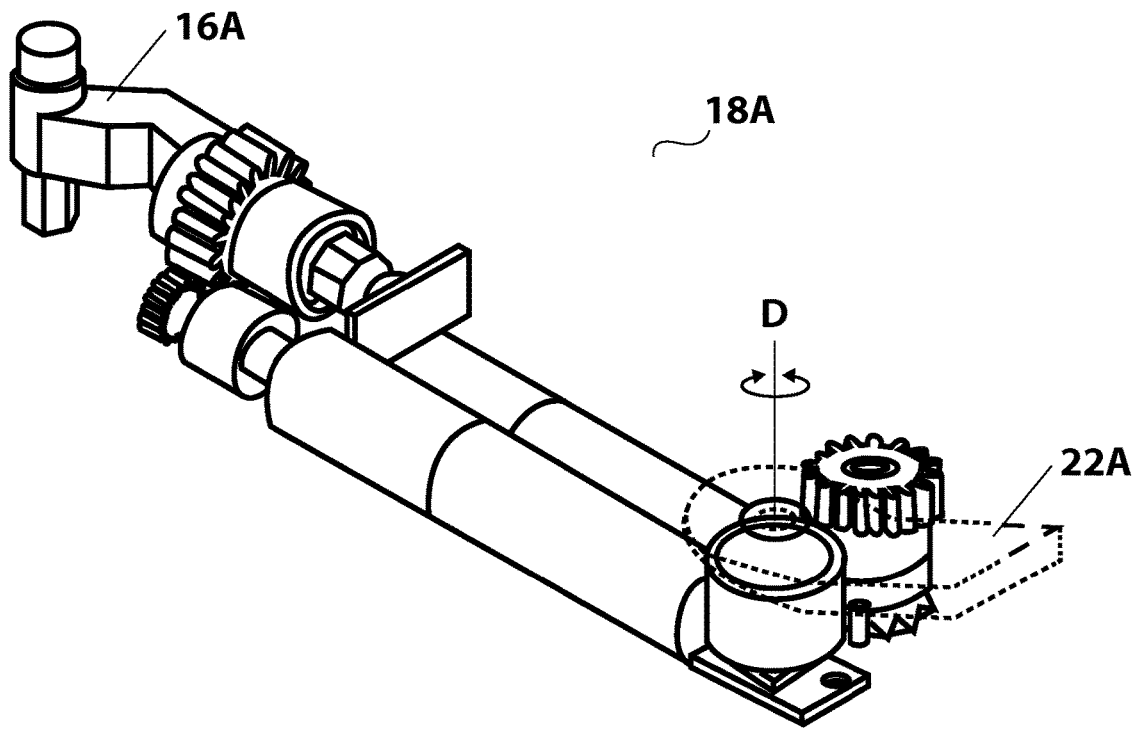
FIG. 3C is a different perspective view of the embodiment of FIG. 3A.
Figure 3D:
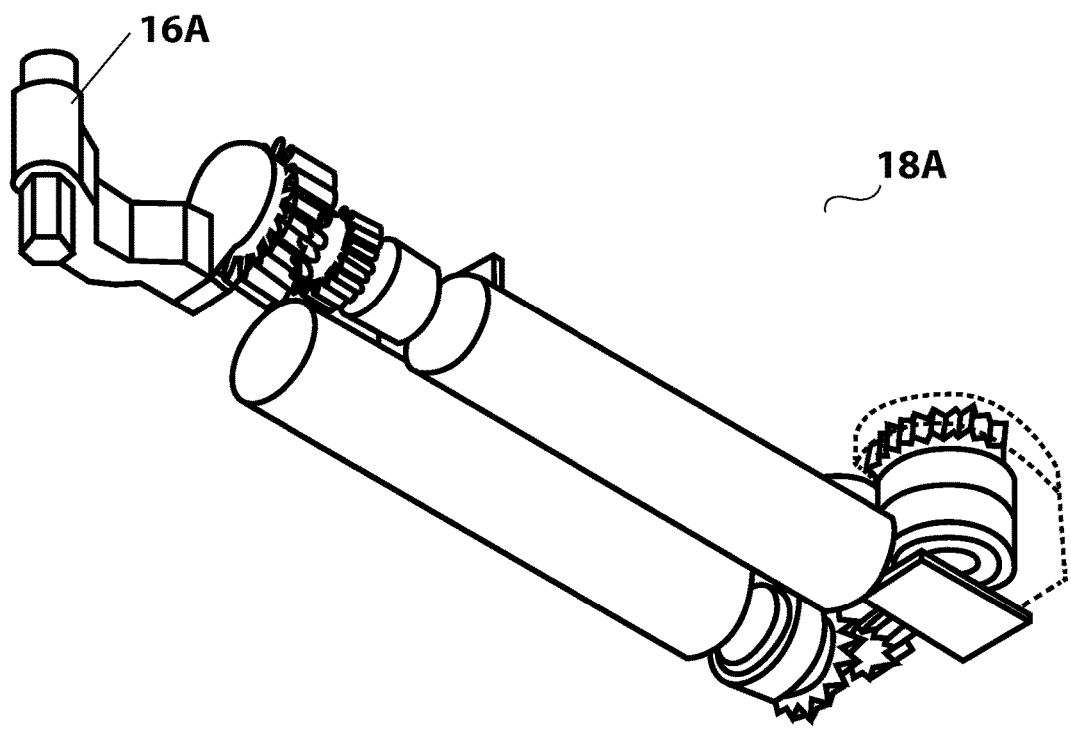
FIG. 3D is a reverse perspective view of the embodiment of FIG. 3A.
Figure 3E:
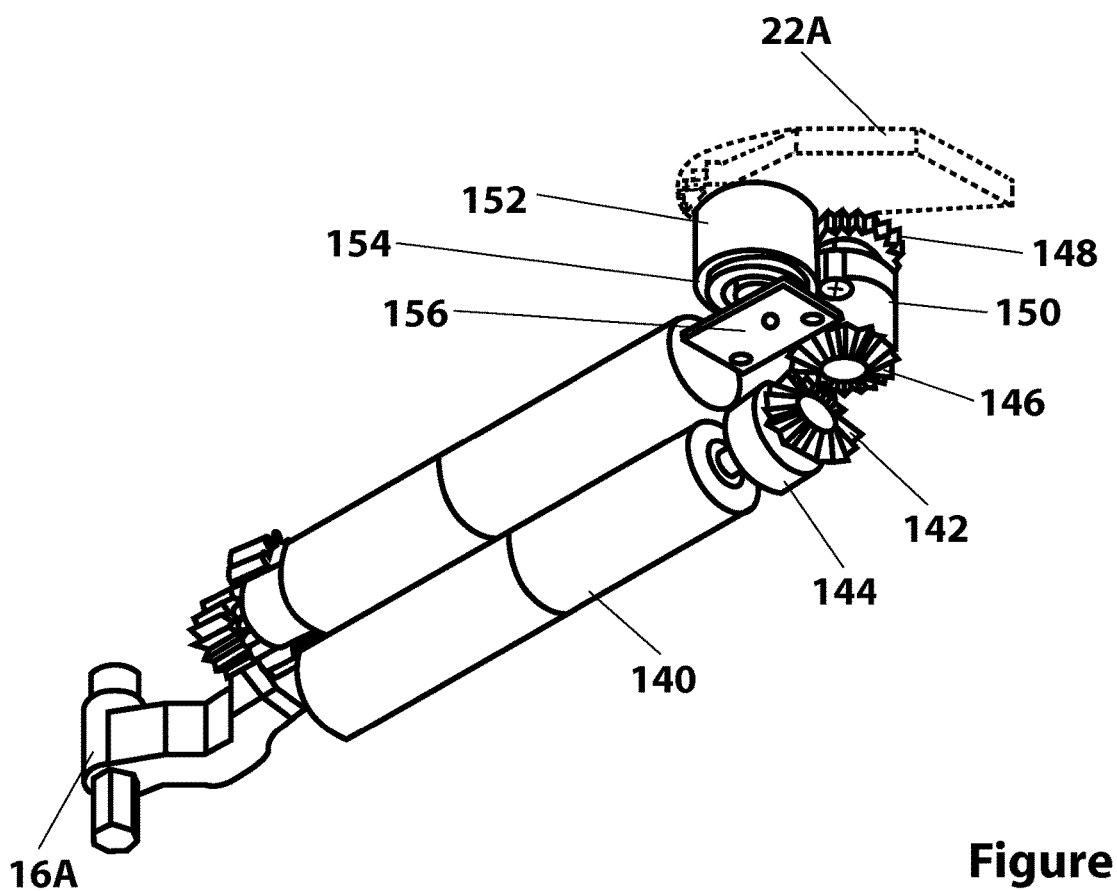
FIG. 3E is an alternate perspective view of medical device as depicted in FIG. 3D.

According to one implementation, certain of the internal components depicted in FIGS. 3A-3E are configured to actuate rotation at the elbow link 22A around axis D (as best shown in FIG. 3C), which is perpendicular to the longitudinal axis of the right upper arm 18A. This rotation around axis D is also referred to as "elbow yaw." The rotation, in one aspect, is created as follows. An actuator 140 is provided that is, in this implementation, a second upper arm motor assembly 140. This motor assembly 140 is operably coupled to the second upper arm motor gear 142, which is a beveled gear in this embodiment. This motor gear 142 is supported by a bearing 144. The motor gear 142 is coupled to the driven gear 146 such that rotation of the motor gear 142 causes rotation of the driven gear 146. The driven gear 146 is fixedly coupled to a link gear 148, which is coupled to the gear teeth 158 (as best shown in FIG. 3B) of the elbow link 22A such that rotation of the driven gear 146 causes rotation of the elbow link 22A around axis D as shown in FIG. 3C. The driven gear 146 and link gear 148 are supported by a bearing pair 150. Further, the elbow link 22A is supported by a bearing pair 152. A magnet holder 154 containing a magnet is also operably coupled to the elbow link 22A. The holder 154 and magnet are operably coupled to a magnetic encoder 156.

According to one embodiment, the additional coupling of the link (or mesh) gear 148 and the elbow link 22A can provide certain advantages, including an additional external reduction (because the gear 148 has fewer gear teeth than the elbow link 22A), shortening of the upper arm 18A and improved joint range of motion. In various embodiments, as with the embodiment shown in FIGS. 4A-E, the robotic devices represent an improvement in range of motion of the elbow joint by reducing the relative distance between the center of the rotational center of the elbow link 22A and the desired direction of travel and preventing physical impediment (as is depicted by arrow A in FIG. 2B).

Figure 4A:
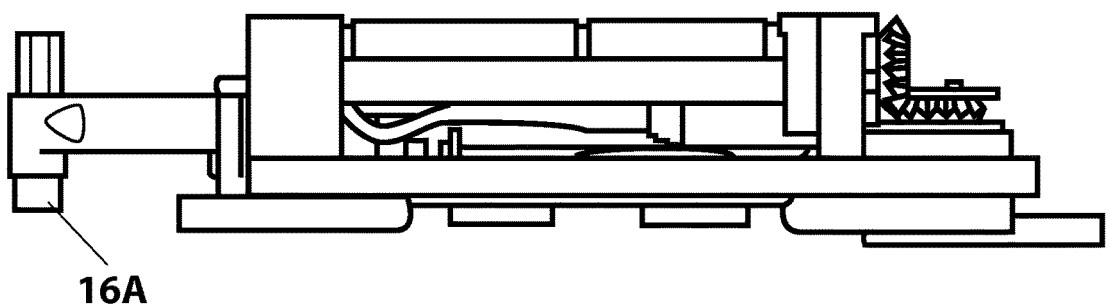
FIG. 4A is a cutaway view of the internal components of the right upper arm of a robotic device, according to one embodiment.
Figure 4B:
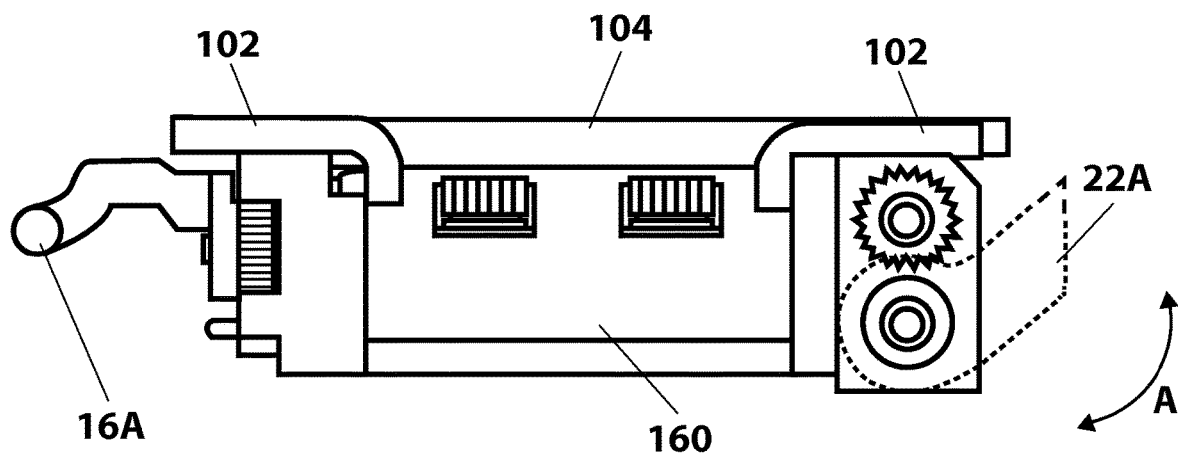
FIG. 4B is a rotated sideview of the embodiment of FIG. 4A.
Figure 4C:
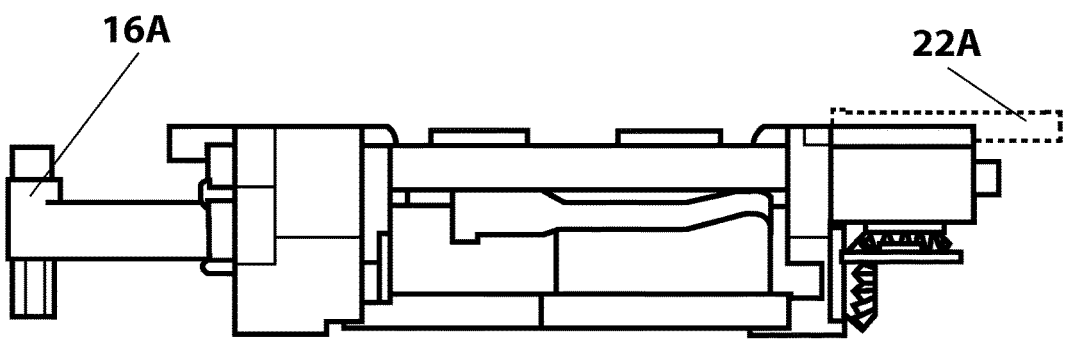
FIG. 4C is a further rotated sideview of the embodiment of FIG. 4A.
Figure 4D:
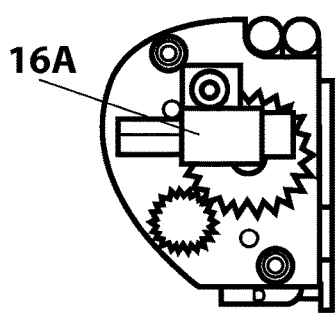
FIG. 4D is an endlong view of the embodiment of FIG. 4A.
Figure 4E:
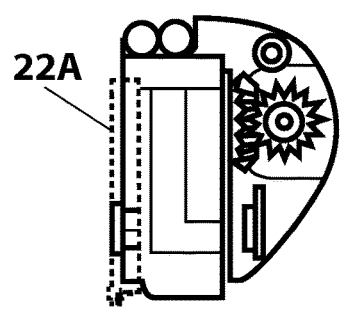
FIG. 4E is a further endlong view of the embodiment of FIG. 4A.

As shown in FIG. 4B, the upper arm 18A can have a rigid-flex PCB 160 positioned therein. In one embodiment, the PCB 160 is operably coupled to and communicate with the actuators 120, 140 and magnetic encoders 132, 156.

According to another embodiment, at least one connection component is associated with the upper arm 18A. More specifically, in this implementation, the power/communication line 102 and the cautery power line 104 enter through a port (not shown) at the proximal end of the upper arm 18A and exit through a port (not shown) at the distal end.

FIGS. 5A-9B depict various embodiments of a right forearm 20A. The various implementations disclosed and depicted herein include the actuators, drive components, and electronics that can be used to accomplish both tool roll and tool drive (open/close action), as will be described in further detail below. As set forth below, the forearm 20A also has two electrically isolated cautery circuits, enabling both bipolar and monopolar cautery end effectors. Certain embodiments are configured to allow for easy removal and replacement of an end effector (a "quick change" configuration). Further embodiments contain sealing elements that help to prevent fluid ingress into the mechanism.

Figure 5A:
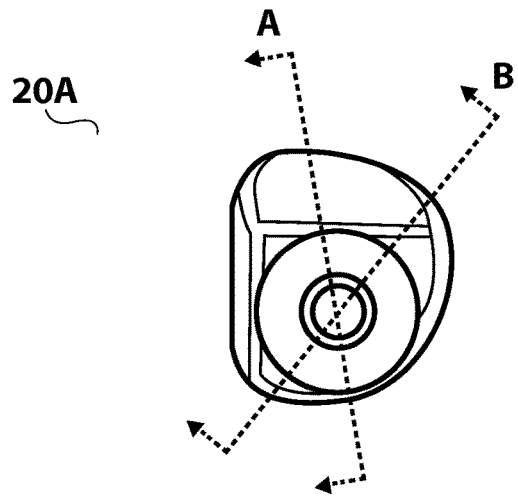
FIG. 5A is a endlong view of the lower arm of a robotic device, according to one embodiment.
Figure 5B:
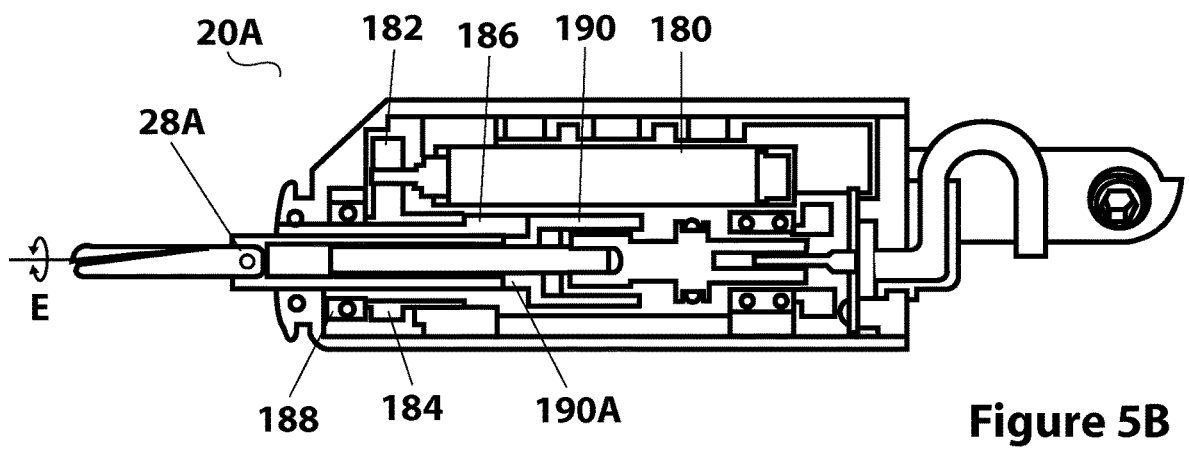
FIG. 5B is cutaway sideview of the internal components of the lower arm of the embodiment of FIG. 5A along line A-A.
Figure 5C:
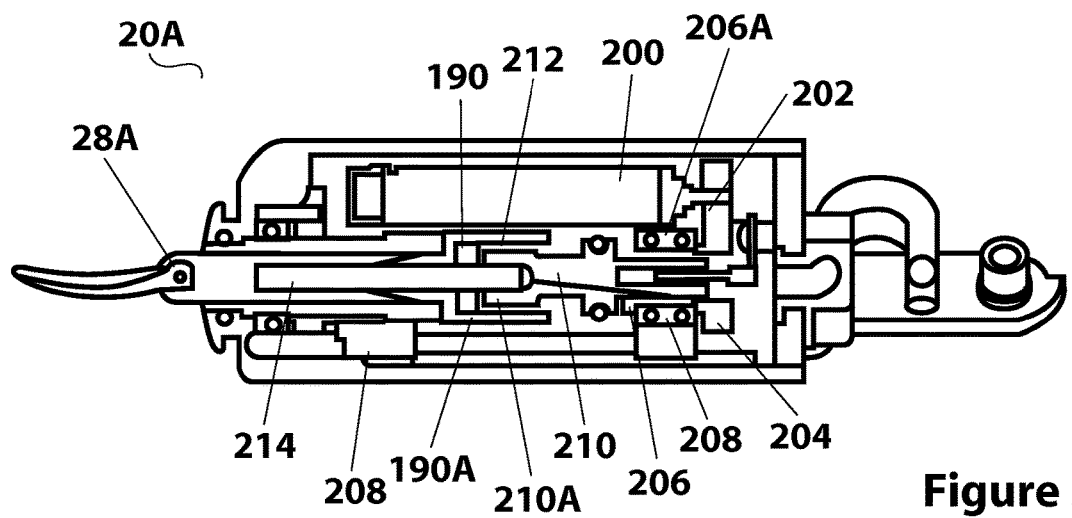
FIG. 5C is cutaway sideview of the internal components of the lower arm of the embodiment of FIG. 5A along line B-B.

According to one implementation, certain of the internal components depicted in FIGS. 5A-5C are configured to actuate rotation at the end effector 28A around axis E (as best shown in FIG. 5B), which is parallel to the longitudinal axis of the right forearm 20A. This rotation around axis E is also referred to as "tool roll." The rotation, in one aspect, is created as follows. An actuator 180 is provided that is, in this implementation, a motor assembly 180. The motor assembly 180 is operably coupled to the motor gear 182, which is a spur gear in this embodiment. The motor gear 182 is coupled to the driven gear 184 such that rotation of the motor gear 182 causes rotation of the driven gear 184. The driven gear 184 is fixedly coupled to the roll hub 186, which is supported by a bearing 188. The roll hub 186 is fixedly coupled to the tool base interface 190, which has external threads 190A which are threadably coupled to the end effector 28A. Thus, rotation of the driven gear 184 causes rotation of the roll hub 186, which causes rotation of the tool base interface 190, which causes rotation of the end effector 28A around axis E as shown in FIG. 5B.

In one embodiment, certain of the internal components depicted in FIGS. 5A-5C are configured to actuate the end effector to open and close. This rotation of the end effector arms such that the end effector opens and closes is also called "tool drive." The actuation, in one aspect, is created as follows. An actuator 200 is provided that is, in this implementation, a motor assembly 200. The motor assembly 200 is operably coupled to the motor gear 202, which is a spur gear in this embodiment. The motor gear 202 is coupled to the driven gear 204 such that rotation of the motor gear 202 causes rotation of the driven gear 204. The driven gear 204 is fixedly coupled to a tool drive nut 206, which is supported by a bearing pair 208. The tool drive nut 206 has a threaded inner lumen 206A, and this threaded inner lumen 206A is threadably coupled to the lead screw 210. More specifically, the outer threads of the lead screw 210 are threadably coupled to the threads on the inner lumen 206A. The lead screw 210 is rotationally coupled to the tool base interface 190 (discussed above). More specifically, the tool base interface 190 has a square-shaped inner lumen 190A, and the distal end of the lead screw 210 has a square-shaped protrusion that fits within the inner lumen 190A, thereby coupling with the tool base interface 190. The distal end of the lead screw 210 can move translationally within the lumen 190A, but cannot rotate in relation to the tool base interface 190, so the lead screw 210 can move translationally in relation to the tool base interface 190, but cannot rotate in relation thereto.

The lead screw 210 also has an insulating sleeve 212 disposed to an external portion of the lead screw 210 and thereby plays a role in maintaining separate electrical cautery channels as will be described below. Further, the lead screw 210 has a threaded inner lumen 210A, which is threadably coupled to the tool pin 214. The tool pin 214 is operationally coupled to a known linkage mechanism within the end effector 28A such that translation of the tool pin 214 causes the grasper arms or blades to open and close. As such, actuation of gear 202 causes rotation of the driven gear 204, which rotates the tool drive nut 206. The rotation of the tool drive nut 206 causes the lead screw 210 to translate as a result of the threadable coupling of the nut 206 and the screw 210. The translation of the screw 210 causes the tool pin 214 to translate, thereby causing the end effector 28A arms or blades to open and close.

In this embodiment, these two axes of rotation are coupled. That is, if pure roll is desired, then the tool open/close drive train must match the speed of the roll train such that there is no relative angular displacement between the tool drive nut 206 and the tool base interface 190.

According to one implementation, the end effector 28A can be quickly and easily coupled to and uncoupled from the forearm 20A in the following fashion. With both the roll and drive axes fixed or held in position, the end effector 28A can be rotated, thereby coupling or uncoupling the threads 190A and 210A. That is, if the end effector 28A is rotated in one direction, the end effector 28A is coupled to the forearm 20A, and if it is rotated in the other direction, the end effector 28A is uncoupled from the forearm 20A.

In accordance with one embodiment, the forearm 20A has two independent cautery channels (referred to herein as "channel A" and "channel B"), which enables the use of either bipolar or monopolar cautery end effectors with this forearm 20A.

Figure 6A:
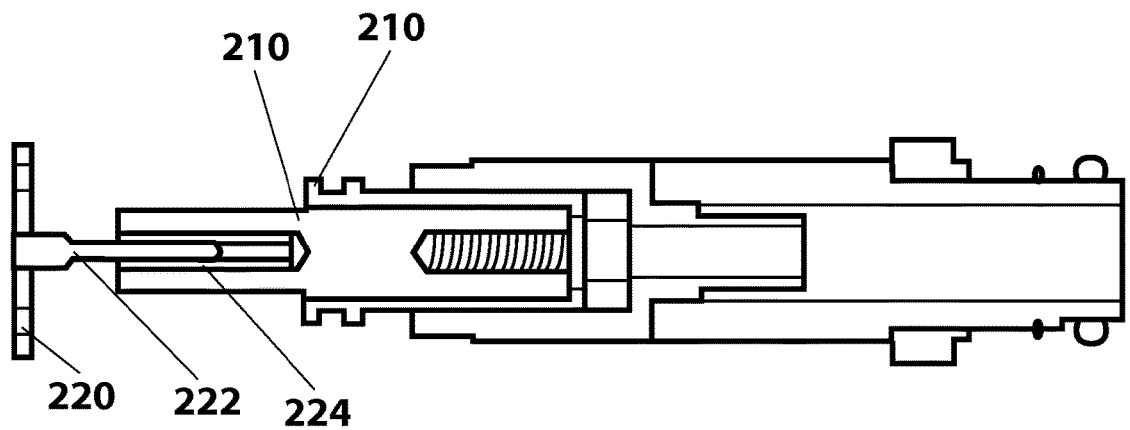
FIG. 6A is a cross-sectional view of the end effector portion of the forearm depicting the electrical portions, according to an exemplary embodiment.

Turning to FIG. 6A, the channel A components of certain exemplary embodiments are set forth in the forearm 20A as shown. A PCB 220 is electrically coupled to lead A of a cautery power line (such as cautery line 104 discussed above) that is coupled to an external power source, such as a cautery generator. The PCB 220 is further electrically coupled to a pin 222, which is electrically coupled to socket 224 (defined in or coupled—electrically and mechanically—to a proximal end of the lead screw 210 discussed above) and is slidably positioned within the socket 224. The lead screw 210 is coupled electrically and mechanically to the end effector pin 214 as best shown in FIG. 5C. As such, energizing lead A in the cautery line 104 energizes channel A in the bipolar cautery end effector 28A. Certain embodiments of the forearm further comprise at least one insulator 225.

Figure 6B:
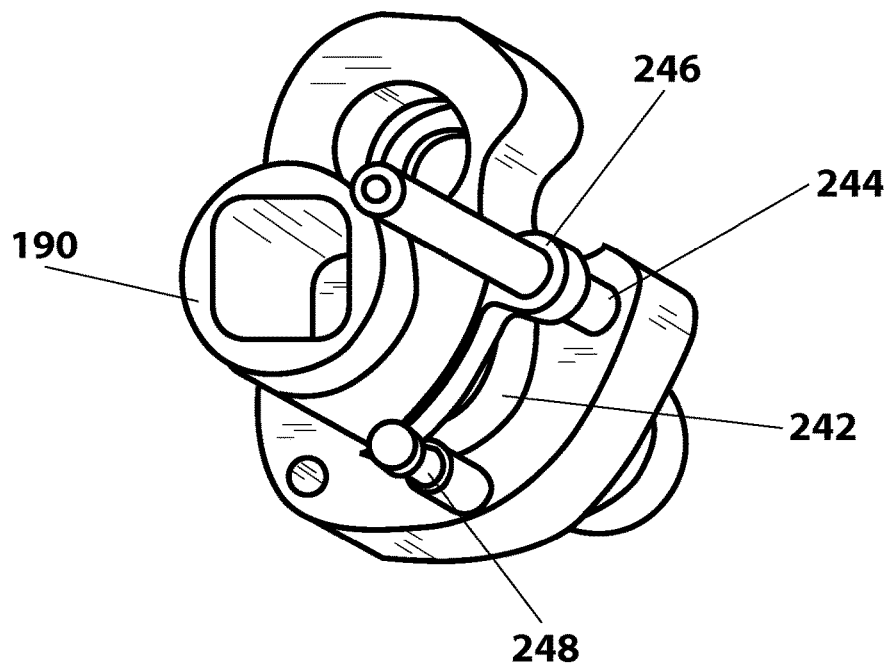
FIG. 6B is a top perspective view of external view of complimentary portion of the forearm to the embodiment of FIG. 6A.
Figure 7:
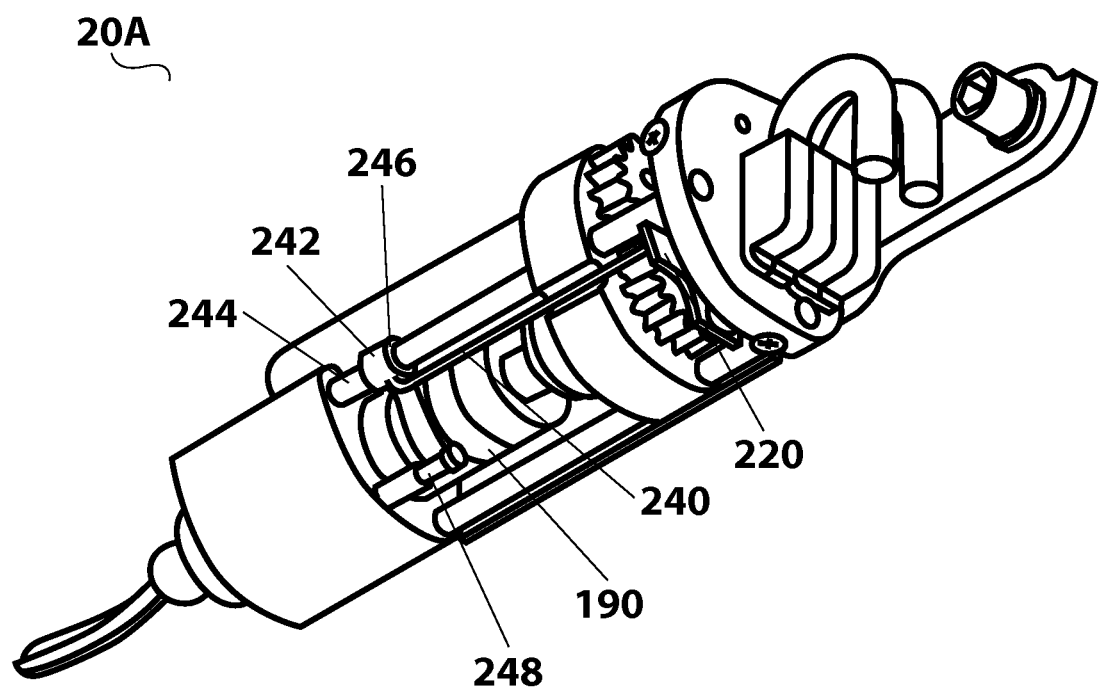
FIG. 7 is a bottom perspective schematic of the internal components of the lower arm of a robotic device, according to one embodiment.

As shown in FIGS. 6B and 7, the channel B components are set forth in the forearm 20A as shown. The PCB 220 discussed above is also electrically coupled to lead B of a cautery power line (such as cautery line 104 discussed above) that is coupled to an external power source. The PCB 220 is further electrically coupled to a conducting rod 240, which is electrically coupled to a wiper 242. The wiper 242 is a tensioned component that supported on one end by a mechanical strut 244. An insulating insert 246 is positioned between the wiper 242 and the mechanical strut 244. At its free end, the wiper 242 is supported by a preloader 248. Based on this configuration, the wiper 242 is loaded or urged—like a leaf spring—against the tool base interface 190 (discussed above) and thus becomes electrically coupled to the tool base interface 190. The tool base interface 190 is mechanically coupled to the end effector 28A and electrically coupled to channel B of that end effector 28A. As such, energizing lead B in the cautery line 104 energizes channel B in the bipolar cautery end effector 28A. In exemplary embodiments, the channel A components are electrically isolated from the channel B components, and both channels are electrically isolated from the chassis to enhance patient safety.

Figure 9A:
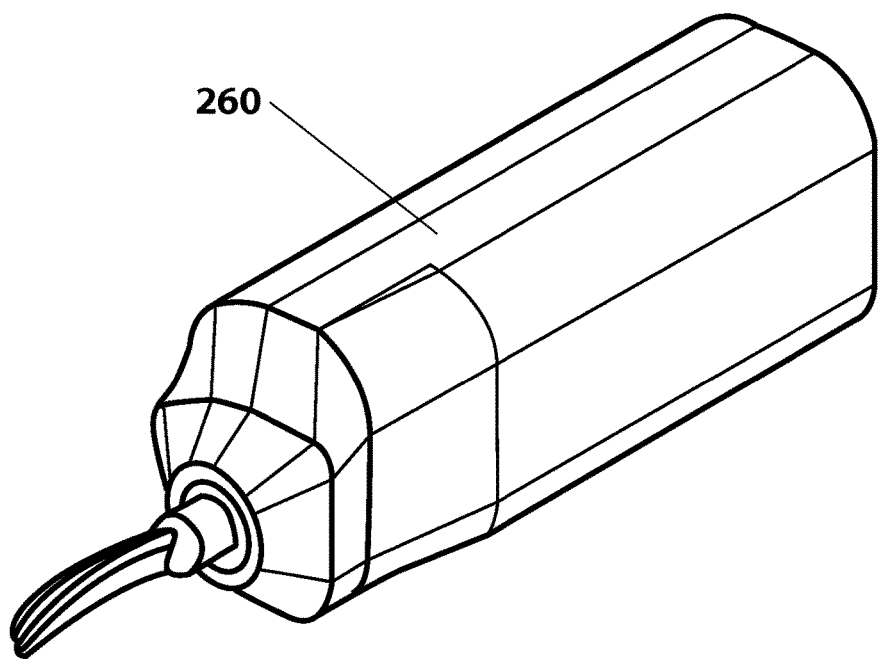
FIG. 9A is a perspective view of the exterior of the forearm according to one embodiment.
Figure 9B:
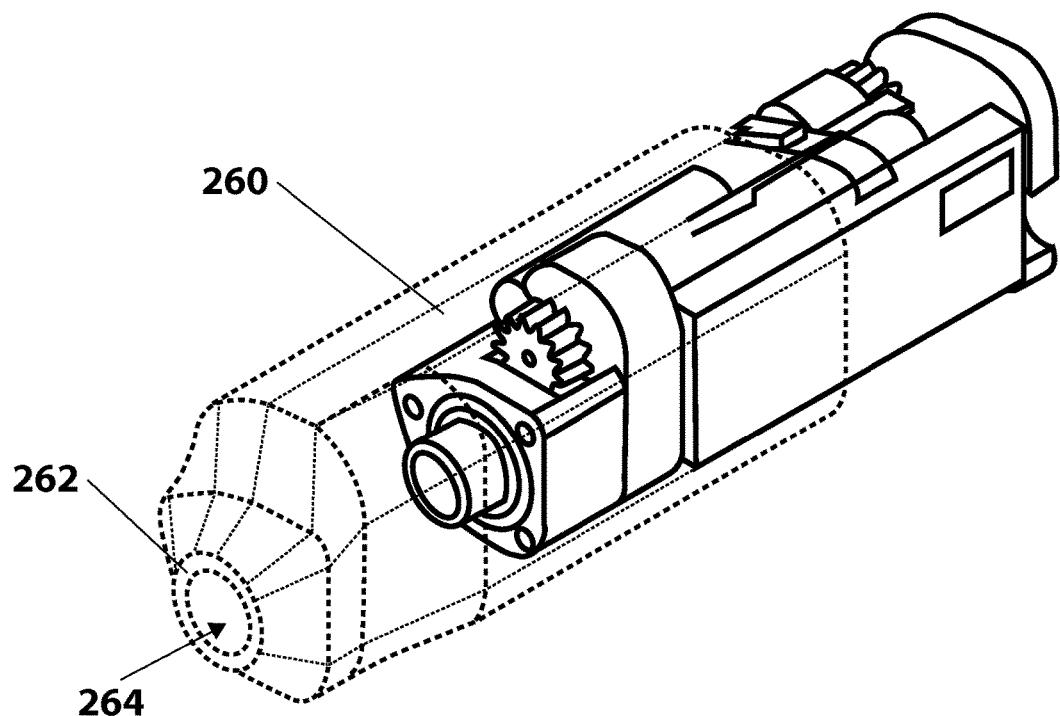
FIG. 9B is an internal view perspective of the embodiment of FIG. 9A

In one implementation, the forearm 20A has at least one fluidic seal interface that helps to prevent fluid ingress into the forearm 20A. One such mechanism is a monolithic single-piece housing 260 as depicted in FIGS. 9A and 9B according to one embodiment. The one-piece nature of the housing 260 greatly reduces the number of interfaces that must be sealed and thus reduces the number of interfaces where fluidic leaks are more likely to occur. The housing 260 is configured to slide over the internal components of the forearm 20A. That is, the proximal end of the housing 260 defines an opening that can be positioned over the forearm 20A (or the forearm 20A is inserted into the lumen) until the housing 260 is correctly positioned over the forearm 20A. As best shown in FIG. 9B, the housing 260 can have an O-ring 262 positioned in a groove defined in the housing 260 around the hole 264 defined in the distal end of the housing 260. The hole 264 is configured to receive the end effector 28A, which in certain embodiments is the distal end of the roll hub 186. In one embodiment, the roll hub 186 (discussed above) is positioned through the hole 264 such that the O-ring 262 is configured to be preloaded against that roll hub 186, thereby forming a fluidic seal between the housing 260 and the external surface of the hub 186, which in certain embodiments may further comprise a stainless steel ring to enhance the seal.

Figure 8A:
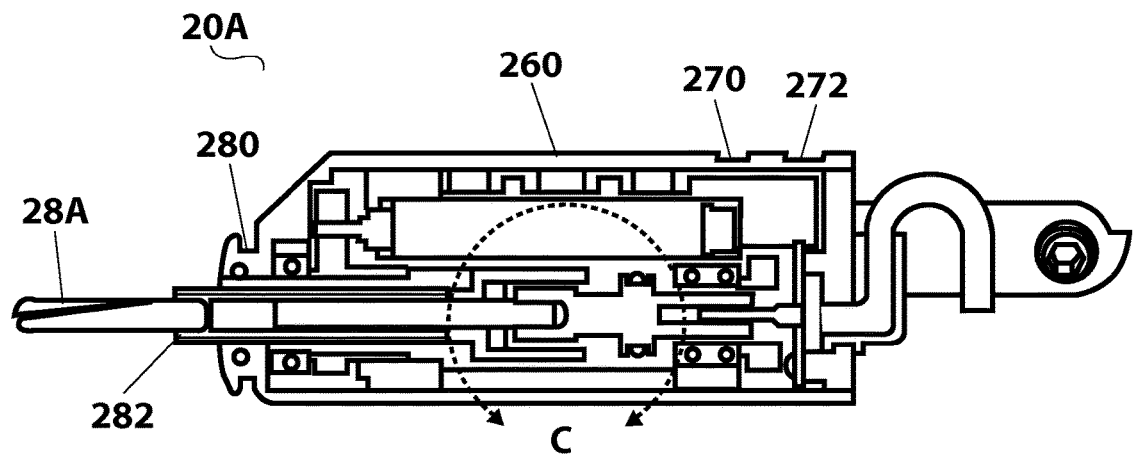
FIG. 8A is cutaway sideview of the internal components of the lower arm of the embodiment of FIG. 5A along line A-A, detailing further electronic components.

In a further embodiment as shown in FIG. 8A, the forearm 20A has two grooves 270, 272 defined in the external portion of the forearm housing 260 (as described above). The grooves 270, 272 can be configured to provide an attachment point for an outer barrier (such as the first barrier 300 described in further detail below) such that an elastic band defined in the opening of the sleeve of the inner barrier 300 can be positioned in the grooves 270, 272, thereby enhancing the coupling of the barrier 300 to the housing 260 and thus enhancing the fluidic seal. In one embodiment, the grooves 270, 272 encircle the entire forearm housing 260. Alternatively, the first barrier 300 can be bonded to the housing 260 via an adhesive or welding. In a further alternative, the housing 260 and the first barrier 300 can be fabricated as a single piece.

According to another implementation as shown in FIG. 8A, the forearm 20A housing 260 can have a groove 280 defined in the housing 260 around the hole 282 in the housing 260 through which the end effector 28A is positioned. The groove 280 can be configured to provide an attachment point for an outer barrier (such as the outer barrier 310 described in further detail below) such that an elastic band defined in the opening of the sleeve of the second barrier 310 can be positioned in the grooves 270, 272, thereby enhancing the coupling of the second barrier 310 to the housing 260 and thus enhancing the fluidic seal.

Figure 8B:
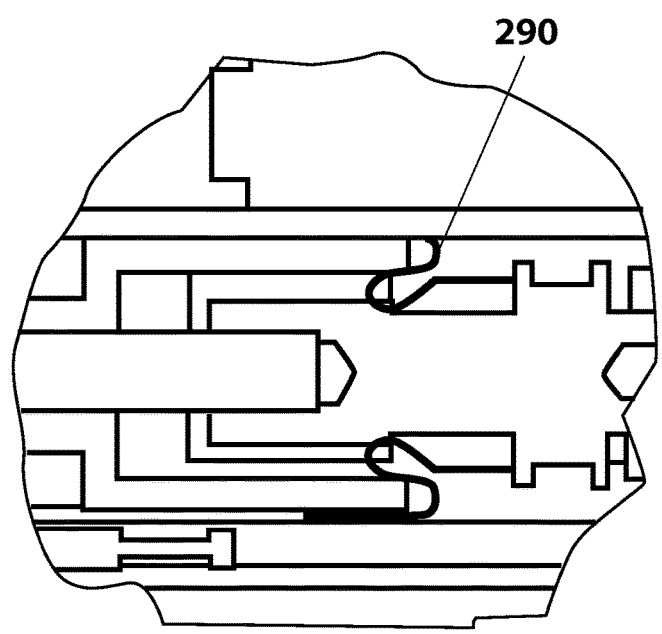
FIG. 8B is a close view of the section C-C of the embodiment of FIG. 8A.

As shown in FIG. 8B, another fluidic seal can be provided according to another embodiment in the form of a flexible membrane 290 that is attached at one end to the lead screw 210 (discussed above) and at the other end to the tool base interface 190 (discussed above). More specifically, the membrane 290 is coupled to the lead screw 210 at the O-ring 292 and is coupled to the tool base interface 190 at the groove 292. In one embodiment, the membrane 290 is retained at the groove 292 with an attachment mechanism such as a cinch (not shown). This membrane 290 serves to provide a fluidic seal for the internal components of the forearm 20A against any external fluids. In one implementation, the seal is maintained whether the end effector 28A is coupled to the forearm 20A or not. Alternatively, the membrane 290 can be replaced with a metallic bellows.

Figure 10A:
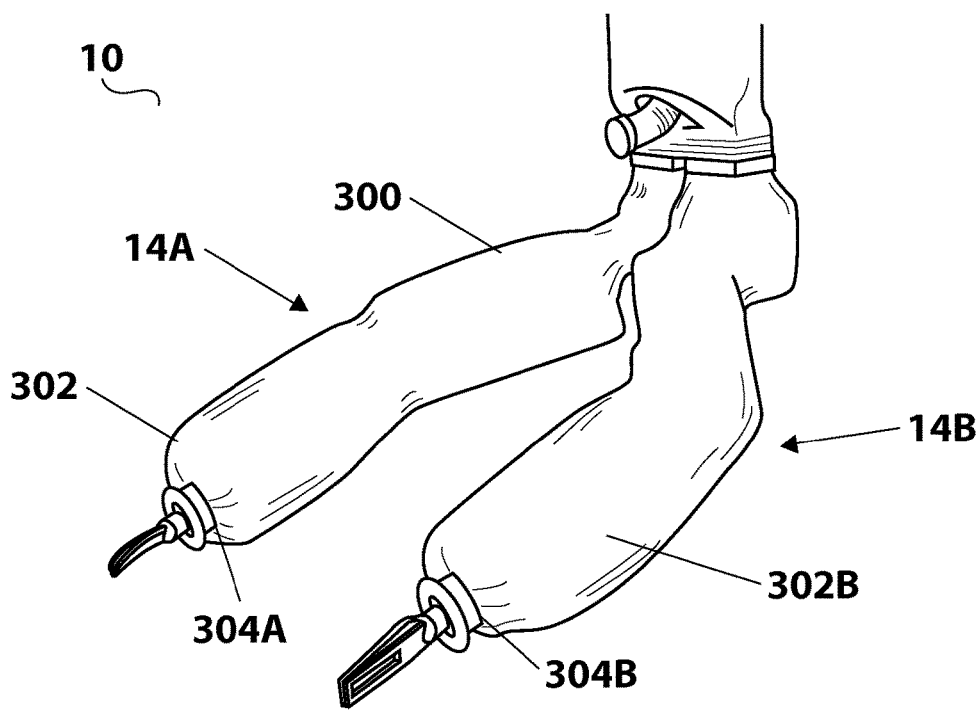
FIG. 10A is a perspective view of one embodiment of the robotic device comprising an inner fluidic seal.
Figure 10B:
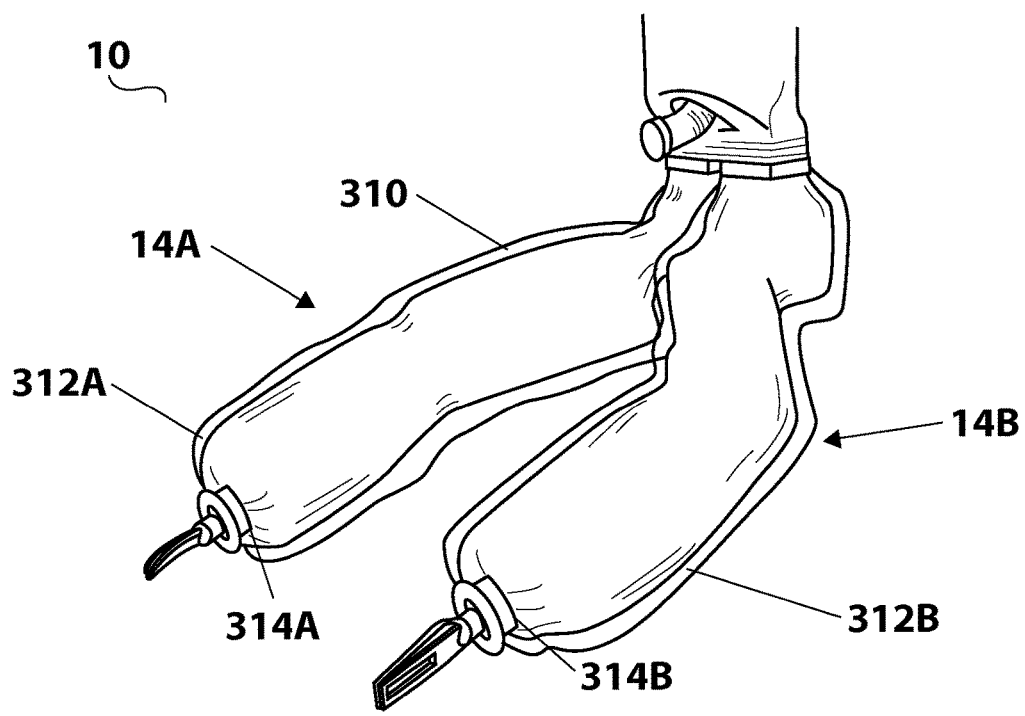
FIG. 10B is a perspective view of the embodiment of FIG. 10A further comprising further outer fluidic seal.

Additional fluidic seals can be provided according to certain embodiments as depicted in FIGS. 10A and 10B. As shown in FIGS. 10A and 10B, the device 10 can have two fluidically sealed barriers protecting each of the device arms 14A, 14B. The first barrier (also referred to herein as an "inner barrier") 300 is shown in FIG. 10A, in which it is positioned around each arm and coupled at the sleeve ends 302A, 302B to the device body 12 via elastic components 304A, 304B that urge the openings in the sleeve ends 302A, 302B, thereby enhancing the fluidic seal. In the embodiment as shown, the elastic components 304A, 304B are positioned around the forearms of the arms 14A at the distal ends of the forearms. Alternatively as described in detail above with respect to FIG. 8A, the elastic components 304A, 304B can be positioned in grooves defined in the forearms (such as grooves 270, 272 described above).

In one embodiment, the inner barrier 300 is a membrane that is permanently bonded to the device 10 and is not removed for the entire operational life of the device 10. The barrier 300 is sterilized with the device 10.

The second barrier (also referred to herein as an "outer barrier") 310 is shown in FIG. 10B, in which is positioned around each arm 14A, 14B, over the inner barrier 300 discussed above, and coupled at the sleeve ends 312A, 312B to the device body 12 via elastic components 314A, 314B that urge the openings at the sleeve ends 312A, 312B against the arms 14A, 14B, thereby enhancing the fluid seal.

Figure 11A:
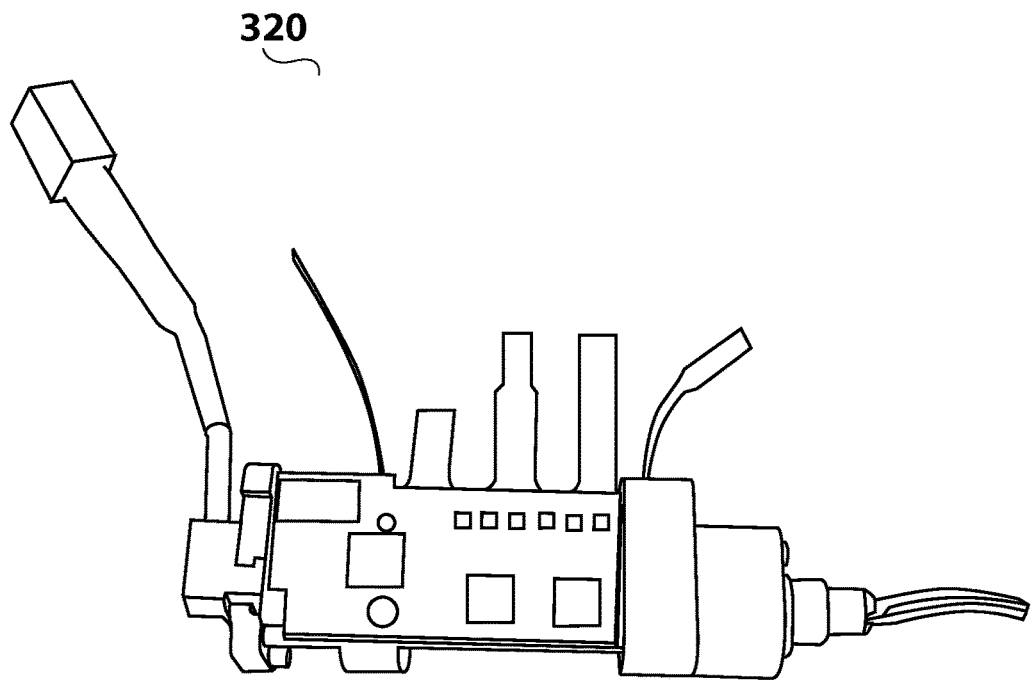
FIG. 11A is a side cutaway view of one embodiment of a rigid-flex PCB component within the forearm of the device.
Figure 11B:
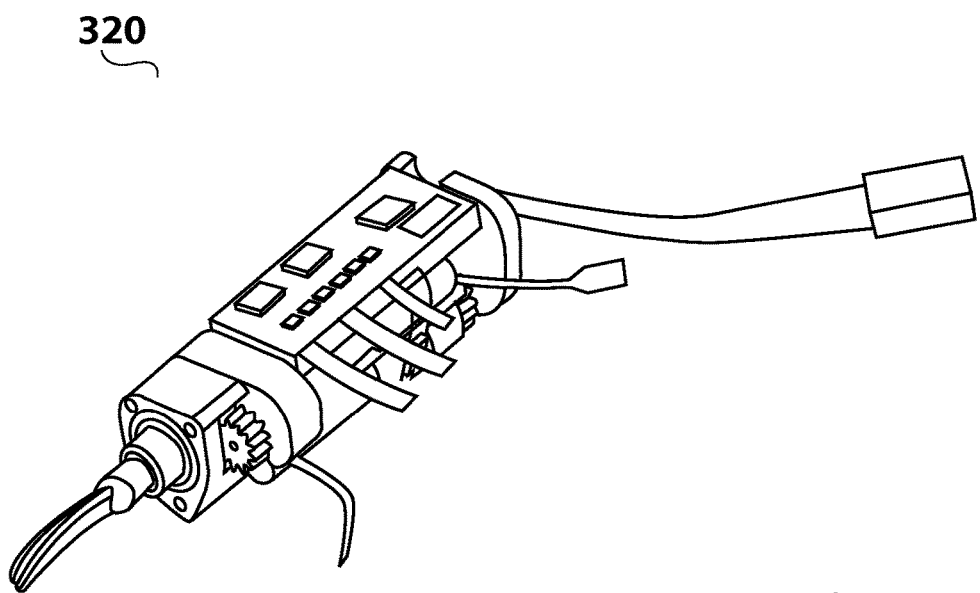
FIG. 11B is a further perspective view of the embodiment of FIG. 11A.
Figure 12A:
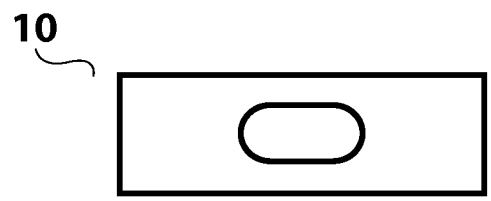
FIG. 12A depicts a top view of a robotic device during insertion, according to one embodiment.
Figure 12B:
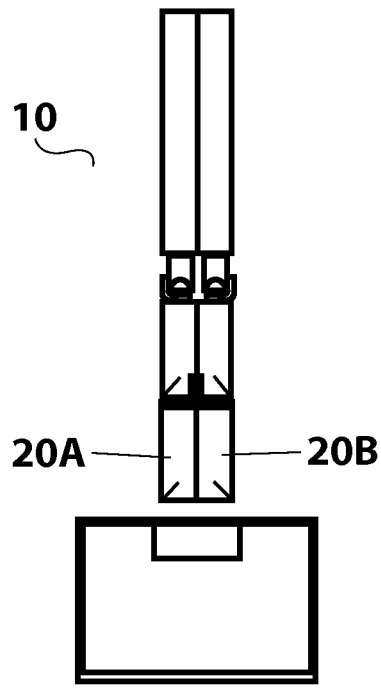
FIG. 12B is a front view of the device of FIG. 12A.
Figure 12C:
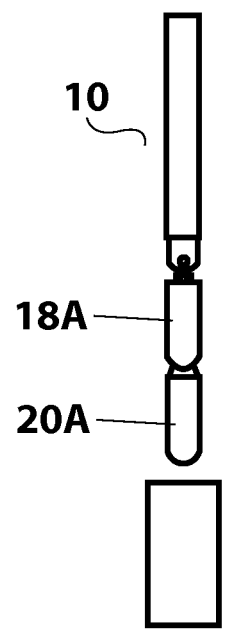
FIG. 12C is a side view of the device of FIG. 12A.
Figure 12D:
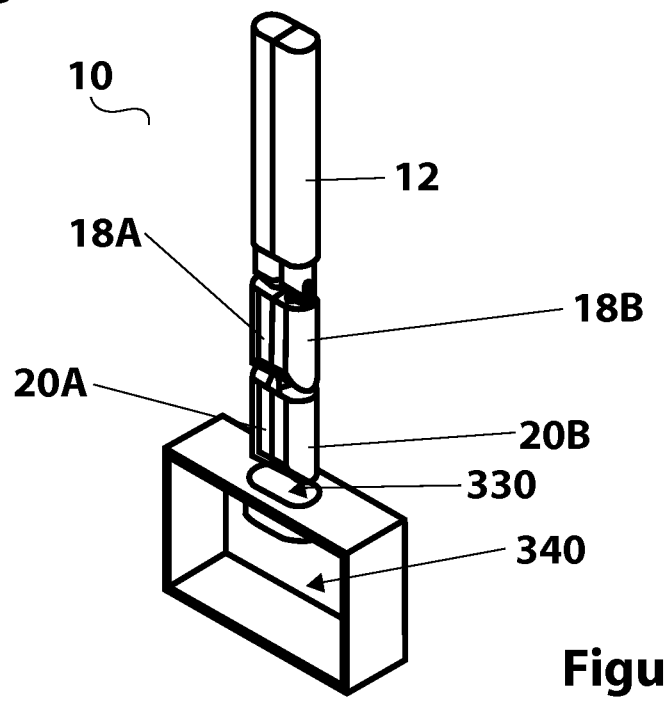
FIG. 12D is a perspective view of the device of FIG. 12A.
Figure 13A:
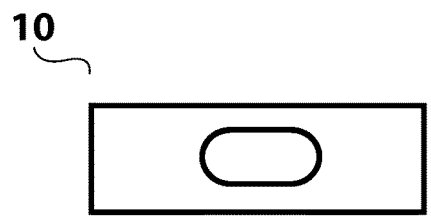
FIG. 13A depicts a top view of a robotic device during insertion, according to one embodiment.
Figure 13B:
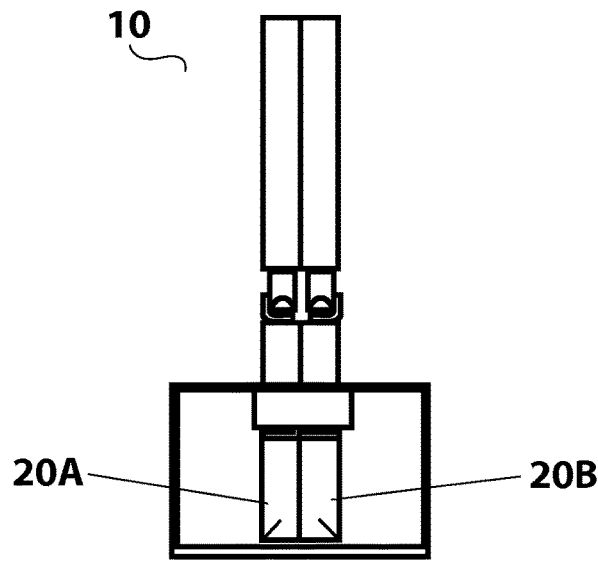
FIG. 13B is a front view of the device of FIG. 13A.
Figure 13C:
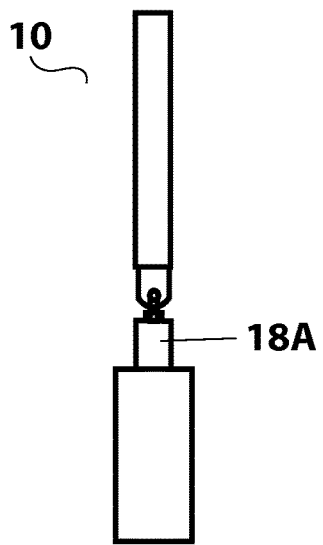
FIG. 13C is a side view of the device of FIG. 13A.
Figure 13D:
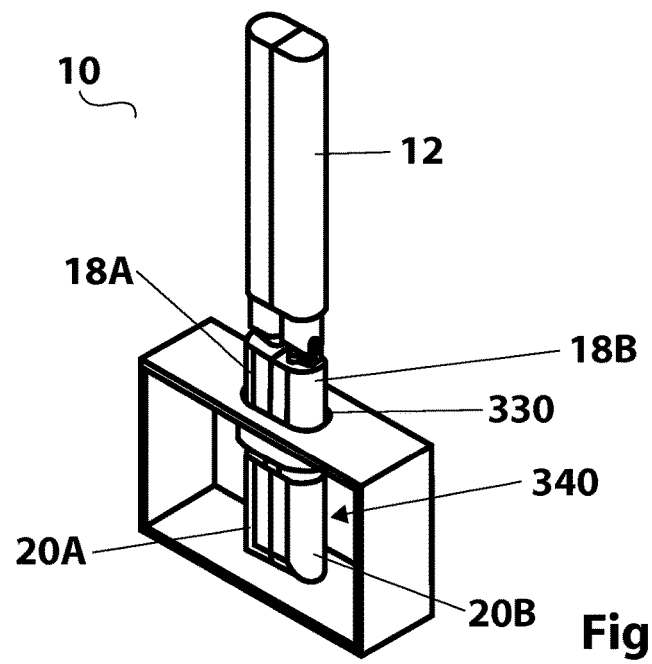
FIG. 13D is a perspective view of the device of FIG. 13A.
Figure 15A:
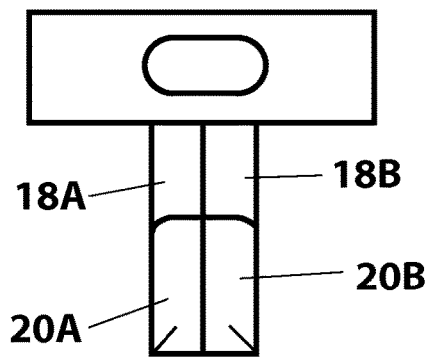
FIG. 15A depicts a top view of a robotic device during insertion, according to one embodiment.
Figure 15B:
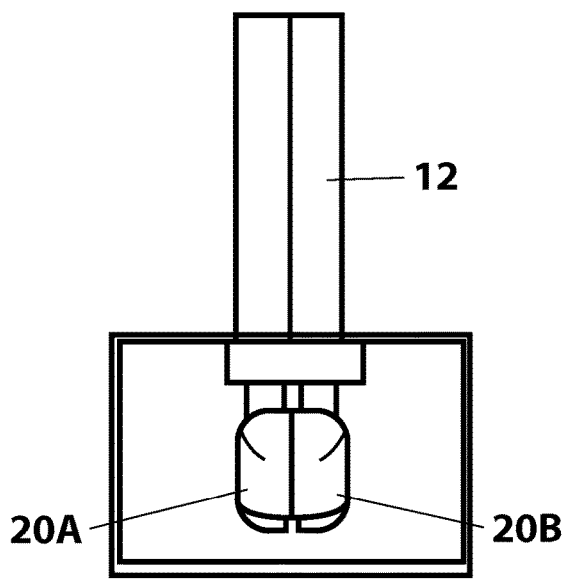
FIG. 15B is a front view of the device of FIG. 15A.
Figure 15C:
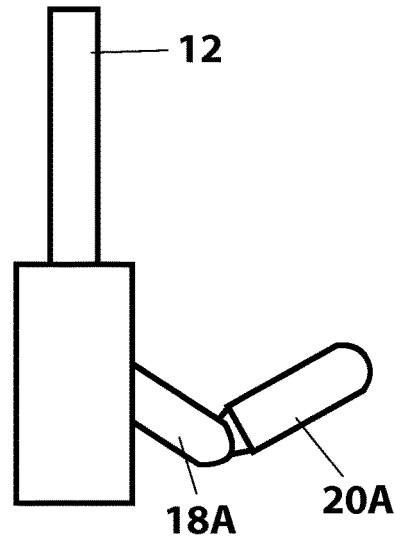
FIG. 15C is a side view of the device of FIG. 15A.
Figure 15D:
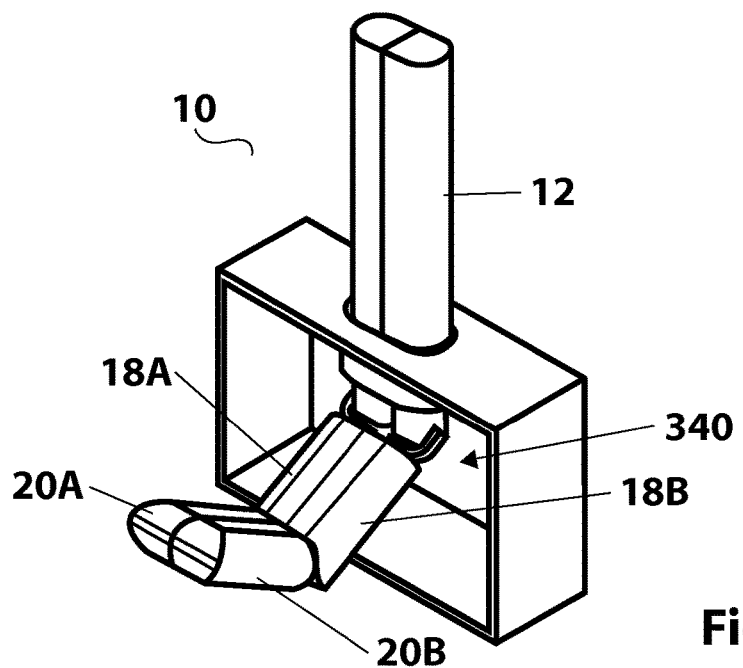
FIG. 15D is a perspective view of the device of FIG. 15A.
Figure 16A:
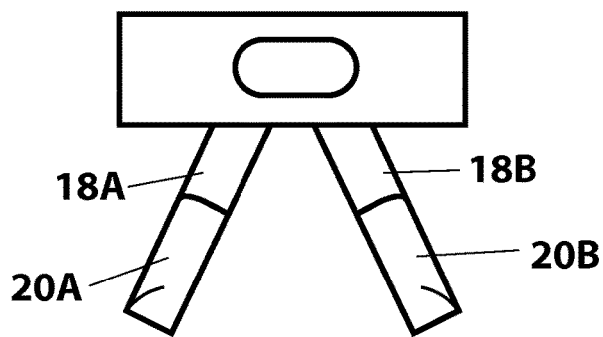
FIG. 16A depicts a top view of a robotic device during insertion, according to one embodiment.
Figure 16B:
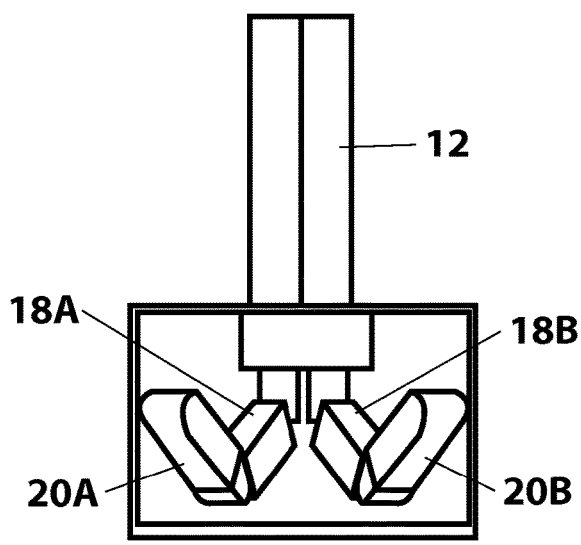
FIG. 16B is a front view of the device of FIG. 16A.
Figure 16C:
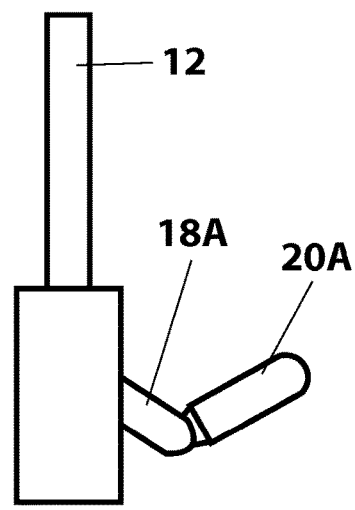
FIG. 16C is a side view of the device of FIG. 16A.
Figure 16D:
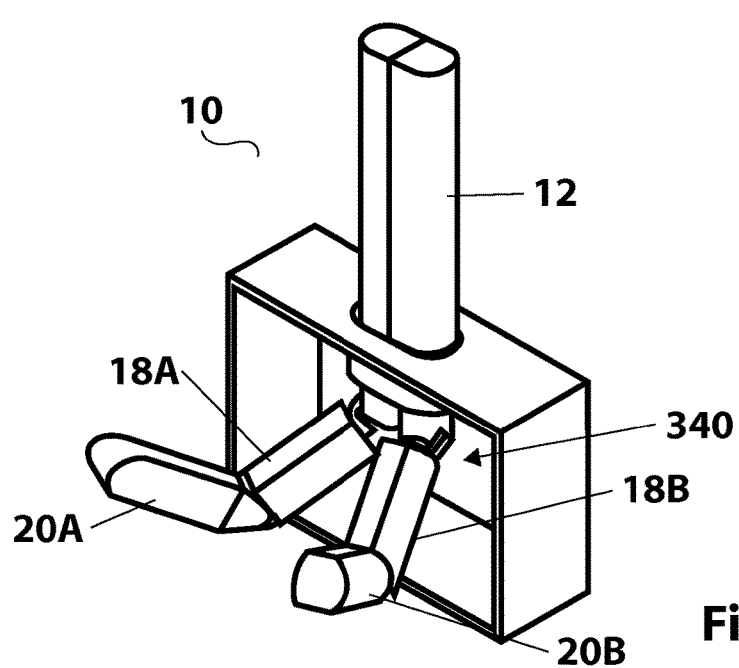
FIG. 16D is a perspective view of the device of FIG. 16A.
Figure 17A:
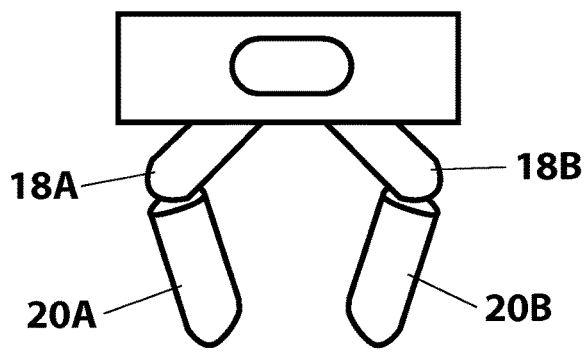
FIG. 17A depicts a top view of a robotic device during insertion, according to one embodiment.
Figure 17B:
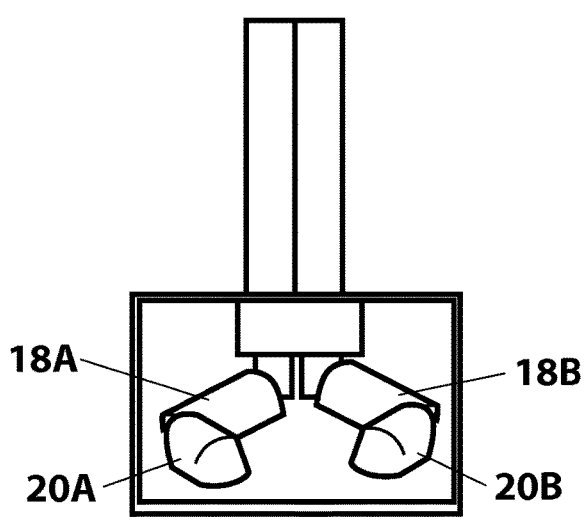
FIG. 17B is a front view of the device of FIG. 17A.
Figure 17C:
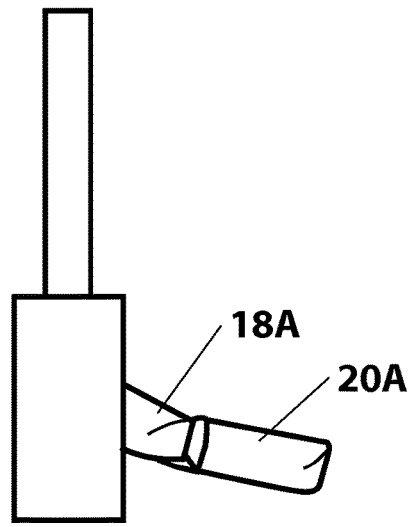
FIG. 17C is a side view of the device of FIG. 17A.
Figure 17D:
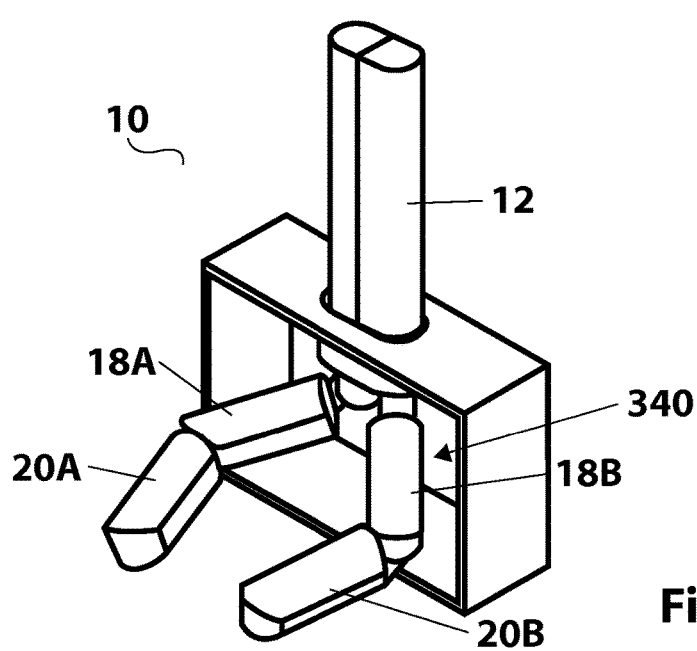
FIG. 17D is a perspective view of the device of FIG. 17A.

FIGS. 11A and 11B depict one embodiment of a rigid-flex PCB component 320 that can be used as the PCB component within the device embodiments described above. It is understood that the rigid-flex assembly is a known fabrication method. In one embodiment, the PCB component 320 that has been assembled using a known fabrication method, but is custom designed and fabricated.

In use as shown in FIGS. 12A-17D, the device embodiments disclosed and contemplated herein are configured to have a consistent cross-section and minimal profile, thereby enhancing the ease of inserting the device through an incision and into a patient's cavity. Further, in one embodiment, the device 10 can be inserted via a specific set of steps that maintain the minimal profile and consistent cross-section in an optimal fashion. As shown in FIG. 12, the device 10 is being prepared to be inserted through the incision 330 and into the cavity 340. Note that the arms 14A, 14B of the device 10 are straight. In FIG. 13, the device 10 is inserted such that the forearms 20A, 20B are positioned in the cavity 340. As shown in FIG. 14, the forearms 20A, 20B can then be rotated as shown to maximize the amount of the device 10 that can be inserted. As the insertion continues as shown in FIG. 15, the upper arms 18A, 18B are also rotated to optimize the surgical space. At this point, the arms 14A, 14B can be moved into their operational position, first by urging them to move in opposite directions as shown in FIG. 16.

Finally, the arms 14A, 14B are rotated so that the elbows are projecting outward in FIG. 17, thereby moving the arms 14A, 14B into their preferred operational position. In exemplary embodiments, the device may be rotated and/or tilted inside the patient relative to the initial insert position, so as to provide the user with access to all four quadrants from the single insertion. Further, as is apparent from the insertion of the device depicted in FIGS. 12A-17D, the arms of the device are inserted in parallel, rather than sequentially, as had been the case in prior surgical robotic devices.

In one implementation, the device 10 has at least one camera that is used in conjunction with the device 10. For example, a camera (not shown) such as a camera having two degrees of freedom (a pan-and-tilt camera) having digital zoom could be used. In one embodiment, it is inserted through the camera lumen 32 defined in the proximal end of the device body 12 as best shown in FIG. 1C. According to one implementation, the camera can be controlled by the user or surgeon using a foot controller and would be easy to remove, clean, and re-insert during a procedure. In another embodiment, the camera can be a standard laparoscope inserted through the same incision, through the lumen 32, or through a different incision.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

We claim:

1. A surgical robotic system for performing surgery on a patient, comprising:
   a. a robotic device sized to be positioned into a cavity of the patient by way of a port positioned in an incision of a patient, the device comprising:
      i. a unitary elongate device body;
      ii. a first shoulder joint movably coupled to a distal end of the device body;
      iii. a second shoulder joint movably coupled to the distal end of the device body;
      iv. a first movable segmented robotic arm operationally connected to the first shoulder joint and comprising:
         A. a first upper arm segment comprising a housing enclosing a plurality of first upper arm actuators;
         B. a first lower arm segment comprising a housing enclosing at least one first lower arm actuator;
         C. a plurality of first arm motor gears and driven gears constructed and arranged to translate movement from the first arm actuators to movement of the first movable segmented robotic arm; and
         D. a first operational component; and
      v. a second movable segmented robotic arm operationally connected to the second shoulder joint and comprising:
         A. a second upper arm segment comprising a housing enclosing a plurality of second upper arm actuators;
         B. a second lower arm segment comprising a housing enclosing at least one second lower arm actuator; and
         C. a plurality of second arm motor gears and driven gears constructed and arranged to translate movement from the second arm actuators to movement of the second movable segmented robotic arm; and
         D. a second operational component; and
   b. a console in electrical communication with the robotic device, the console configured to control the robotic device from outside the patient,
   wherein:
   a. the unitary device body is configured to be inserted into the port such that the distal end is within the cavity and at least a portion of the device body is external to the cavity,
   b. the first and second moveable segmented arms are capable of being positioned substantially parallel with a longitudinal axis of the device body for insertion by way of the port, and
   c. the first and second lower arm lower arm actuators are constructed and arranged to tool roll and tool drive the first and second operational components.

2. The surgical robotic system of claim 1, wherein the robotic device comprises at least one actuator for operation, rotation or movement of at least one of the first shoulder, the second shoulder, the first segmented arm, the second segmented arm, the first operational component, and the second operational component.

3. The surgical robotic system of claim 2, wherein the at least one actuator is a brushless DC motor.

4. The surgical robotic system of claim 3, wherein the device body further comprises a rigid-flex PCB in operational communication with the actuator and configured to perform yaw and pitch functions.

5. The surgical robotic system of claim 1, wherein the first movable segmented robotic arm further comprises:
   a. a first upper arm segment;
   b. a first elbow joint; and
   c. a first lower arm segment,
   wherein the first upper arm segment is configured to be capable of roll, pitch and yaw relative to the first shoulder joint and the first lower arm is configured to be capable of yaw relative to the first upper arm by way of the elbow joint.

6. The surgical robotic system of claim 5, wherein the first operational component is chosen from a group consisting of a grasping component, a cauterizing component, a suturing component, an imaging component, an irrigation component, a suction component, an operational arm component, a sensor component, and a lighting component.

7. The surgical robotic system of claim 5, wherein the second operational component is chosen from a group consisting of a grasping component, a cauterizing component, a suturing component, an imaging component, an irrigation component, a suction component, an operational arm component, a sensor component, and a lighting component.

8. A surgical robotic system for performing minimally-invasive surgery on a patient, comprising:
   a. a robotic device sized to be positioned into a patient body cavity, the device comprising:
      i. an elongate device body constructed and sized to be positioned through an incision and into the body cavity of the patient;
      ii. a first shoulder joint movably coupled to a distal end of the device body;
      iii. a second shoulder joint movably coupled to the distal end of the device body;
      iv. a first movable segmented robotic arm operationally connected to the first shoulder joint and comprising:
         A. a first upper arm segment comprising a housing enclosing a plurality of first upper arm actuators;
         B. a first lower arm segment comprising a housing enclosing at least one first lower arm actuator;
         C. a plurality of first arm motor gears and driven gears constructed and arranged to translate movement from the first arm actuators to movement of the first movable segmented robotic arm; and
         D. a first operational component; and
      v. a second movable segmented robotic arm operationally connected to the second shoulder joint and comprising:
         A. a second upper arm segment comprising a housing enclosing a plurality of second upper arm actuators;
         B. a second lower arm segment comprising a housing enclosing at least one second lower arm actuator; and
         C. a plurality of second arm motor gears and driven gears constructed and arranged to translate movement from the second arm actuators to movement of the second movable segmented robotic arm; and
         D. a second operational component; and
   b. a console for control of the robotic device from outside the patient by way of a port positioned in the incision, the console in electrical communication with the robotic device.

9. The surgical robotic system of claim 8, wherein:
   a. the first lower robotic arm segment comprises a first elbow joint,
   b. the second lower robotic arm segment comprises a second elbow joint,
   c. the first lower arm and second lower arm are configured to be capable of yaw relative to the upper arm by way of the first and second elbow joints, and
   d. the first and second moveable segmented arms are capable of being positioned substantially parallel with a longitudinal axis of the device body for insertion by way of the port.

10. The surgical robotic system of claim 9, wherein at least one actuator is configured for rotation or movement of at least one of the first shoulder joint, the second shoulder joint, the first upper robotic arm segment, the second upper robotic arm segment, the first lower robotic arm segment, the second lower robotic arm segment, the first operational component, and the second operational component.

11. The surgical robotic system of claim 9, wherein the first operational component is chosen from a group consisting of a grasping component, a cauterizing component, a suturing component, an imaging component, an irrigation component, a suction component, an operational arm component, a sensor component, and a lighting component.

12. The surgical robotic system of claim 9, wherein the second operational component is chosen from a group consisting of a grasping component, a cauterizing component, a suturing component, an imaging component, an irrigation component, a suction component, an operational arm component, a sensor component, and a lighting component.

13. A minimally invasive surgery system, comprising:
   a. a robotic device comprising:
      i. an elongate device body having proximal and distal ends and being constructed and sized to be positioned through an incision and into the body cavity of the patient;
      ii. a first movable segmented robotic arm operationally connected to the first shoulder joint and comprising:
         A. a first shoulder joint movably coupled to a distal end of the device body;
         B. a first upper arm segment comprising a housing enclosing a plurality of first upper arm actuators;
         C. a first elbow joint;
         D. a first lower arm segment comprising a housing enclosing at least one first lower arm actuator;
         E. a plurality of first arm motor gears and driven gears constructed and arranged to translate movement from the first arm upper and lower actuators to movement of the first movable segmented robotic arm; and
         F. a first operational component; and
      iii. a second movable segmented robotic arm operationally connected to the second shoulder joint and comprising:
         A. a second shoulder joint movably coupled to the distal end of the device body;
         B. a second upper arm segment comprising a housing enclosing a plurality of second upper arm actuators;
         C. a second elbow joint;
         D. a second lower arm segment comprising a housing enclosing at least one second lower arm actuator; and
         E. a plurality of second arm motor gears and driven gears constructed and arranged to translate movement from the second arm upper and lower actuators to movement of the second movable segmented robotic arm; and
         F. a second operational component;
   wherein the robotic device is constructed and arranged for insertion and operation via:
   a. positioning the first and second moveable segmented arms substantially in line with a longitudinal axis of the device body prior to insertion into a body cavity of a patient,
   b. inserting the distal end of the robotic device into the body cavity of the patient through a port in communication with the body cavity such that the first and second movable segmented robotic arms are disposed entirely within the body cavity and the elongate device body is disposed in the port such that the distal end of the device body is disposed within the body cavity and the proximal end of the device body is disposed outside the body cavity, and c. rotating the first and second moveable segmented arms such that the first and second elbow joints project outward from the longitudinal axis.

14. The system of claim 13, wherein the device is constructed and arranged to be rotated and/or tilted inside the patient relative to the initial insert position.

15. The system of claim 13, wherein the first and second moveable segmented arms are constructed and arranged for performing yaw and pitch functions.

16. The system of claim 13, wherein the device body further comprises a first rigid-flex PCB in operational communication with the first movable segmented robotic arm and a second rigid-flex PCB in operational communication with the second movable segmented robotic arm.

17. The surgical robotic system of claim 13, wherein the first and second upper arm segments are constructed and arranged to be capable of roll, pitch and yaw relative to the first and second shoulder joints, respectively, and the first and second lower arm segments are configured to be capable of yaw relative to the first and second upper arm segments by way of the first and second elbow joints, respectively.

18. The surgical robotic system of claim 13, further comprising at least one absolute position sensor comprising a magnetic encoder.

* * * * *